(12) United States Patent
Migliazza et al.

(10) Patent No.: US 8,900,295 B2
(45) Date of Patent: Dec. 2, 2014

(54) PROSTHETIC VALVE WITH VENTRICULAR TETHERS

(71) Applicant: Edwards Lifesciences Corporation, Irvine, CA (US)

(72) Inventors: John F. Migliazza, Irvine, CA (US); Hugues LaFrance, Mission Viejo, CA (US); Harvey H. Chen, Irvine, CA (US); Travis Zenyo Oba, Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/626,732

(22) Filed: Sep. 25, 2012

(65) Prior Publication Data

US 2013/0079873 A1    Mar. 28, 2013

Related U.S. Application Data

(60) Provisional application No. 61/539,356, filed on Sep. 26, 2011.

(51) Int. Cl.
*A61F 2/24* (2006.01)
*A61B 17/04* (2006.01)
*A61B 17/06* (2006.01)

(52) U.S. Cl.
CPC ........... *A61F 2/2412* (2013.01); *A61B 17/0401* (2013.01); *A61B 2017/0464* (2013.01); *A61B 2017/0417* (2013.01); *A61B 2017/0437* (2013.01); *A61B 2017/0496* (2013.01); *A61B 2017/0441* (2013.01); *A61F 2/2457* (2013.01); *A61F 2/2418* (2013.01); *A61B 17/0487* (2013.01); *A61F 2250/0007* (2013.01); *A61F 2/2409* (2013.01); *A61B 2017/06176* (2013.01)
USPC ....... 623/2.19; 623/2.36; 623/2.41; 623/2.13; 623/2.14; 623/2.15; 623/2.17; 623/2.18; 623/2.37; 623/2.38

(58) Field of Classification Search
USPC ......................................................... 623/2.19
See application file for complete search history.

(56) References Cited

U.S. PATENT DOCUMENTS 4,055,861 A    11/1977   Carpentier et al.
5,041,130 A     8/1991   Cosgrove et al.

(Continued)

FOREIGN PATENT DOCUMENTS

WO    91/19465 A1     12/1991
WO    2005/004753 A1   1/2005
WO    2007/131513 A1  11/2007

OTHER PUBLICATIONS

Cochran, et al., Effect of Papillary Muscle Position on Mitral Valve Function: Relationship to Homografts, The Society of Thoracic Surgeons, pp. S155-S161, 1998.

(Continued)

*Primary Examiner* — David Isabella
*Assistant Examiner* — Jacqueline Woznicki
(74) *Attorney, Agent, or Firm* — AnneMarie Kaiser; Pui Tong Ho; Guy Cumberbatch

(57) ABSTRACT

A prosthetic valve assembly and method of implanting same is disclosed. The prosthetic valve assembly includes a prosthetic valve formed by support frame and valve leaflets, with one or more tethers each having a first end secured to the support frame and the second end attached to, or configured for attachment to, to papillary muscles or other ventricular tissue. The tether is configured and positioned so as to avoid contact or other interference with movement of the valve leaflets, while at the same time providing a tethering action between the support frame and the ventricular tissue. The valve leaflets may be flexible (e.g., so-called tissue or synthetic leaflets) or mechanical.

13 Claims, 17 Drawing Sheets

(56) References Cited

U.S. PATENT DOCUMENTS

| | | |
|---|---|---|
| 5,662,704 A | 9/1997 | Gross |
| 6,050,936 A | 4/2000 | Schweich, Jr. et al. |
| 6,312,464 B1 | 11/2001 | Navia |
| 6,332,864 B1 | 12/2001 | Schweich, Jr. et al. |
| 6,332,893 B1 | 12/2001 | Mortier et al. |
| 6,406,420 B1 | 6/2002 | McCarthy et al. |
| 6,409,759 B1 | 6/2002 | Peredo |
| 6,558,416 B2 | 5/2003 | Cosgrove et al. |
| 6,723,038 B1 | 4/2004 | Schroeder et al. |
| 6,764,510 B2 | 7/2004 | Vidlund et al. |
| 6,797,002 B2 | 9/2004 | Spence et al. |
| 7,101,395 B2 | 9/2006 | Tremulis et al. |
| 7,112,219 B2 | 9/2006 | Vidlund et al. |
| 7,166,126 B2 | 1/2007 | Spence et al. |
| 7,166,127 B2 | 1/2007 | Spence et al. |
| 7,189,199 B2 | 3/2007 | McCarthy et al. |
| 7,247,134 B2 | 7/2007 | Vidlund et al. |
| 7,431,692 B2 | 10/2008 | Zollinger et al. |
| 7,591,847 B2 | 9/2009 | Navia et al. |
| 7,776,084 B2 | 8/2010 | Johnson |
| 7,871,435 B2 | 1/2011 | Carpentier et al. |
| 8,206,439 B2 | 6/2012 | Gomez Duran |
| 2002/0029080 A1* | 3/2002 | Mortier et al. ............... 623/2.36 |
| 2003/0078653 A1 | 4/2003 | Vesely et al. |
| 2003/0105519 A1 | 6/2003 | Fasol et al. |
| 2004/0186566 A1 | 9/2004 | Hindrichs et al. |
| 2005/0070999 A1* | 3/2005 | Spence ........................ 623/2.37 |
| 2005/0075727 A1 | 4/2005 | Wheatley |
| 2005/0197696 A1 | 9/2005 | Gomez Duran |
| 2006/0030885 A1 | 2/2006 | Hyde |
| 2006/0195183 A1 | 8/2006 | Navia et al. |
| 2006/0259135 A1 | 11/2006 | Navia et al. |
| 2006/0281968 A1 | 12/2006 | Duran et al. |
| 2007/0016291 A1* | 1/2007 | Johnson ....................... 623/2.41 |
| 2007/0038294 A1 | 2/2007 | Navia |
| 2007/0049952 A1 | 3/2007 | Weiss |
| 2007/0050020 A1 | 3/2007 | Spence |
| 2007/0066863 A1 | 3/2007 | Rafiee et al. |
| 2007/0100439 A1 | 5/2007 | Cangialosi et al. |
| 2007/0118151 A1 | 5/2007 | Davidson |
| 2007/0123979 A1 | 5/2007 | Perier et al. |
| 2007/0162111 A1 | 7/2007 | Fukamachi et al. |
| 2007/0173930 A1 | 7/2007 | Sogard et al. |
| 2007/0213582 A1 | 9/2007 | Zollinger et al. |
| 2007/0255396 A1 | 11/2007 | Douk et al. |
| 2009/0043381 A1 | 2/2009 | Macoviak et al. |
| 2010/0023117 A1 | 1/2010 | Yoganathan et al. |
| 2010/0063586 A1 | 3/2010 | Hasenkam et al. |
| 2011/0190879 A1 | 8/2011 | Bobo et al. |
| 2012/0078357 A1* | 3/2012 | Conklin ....................... 623/2.18 |
| 2013/0116780 A1* | 5/2013 | Miller et al. ................. 623/2.36 |

OTHER PUBLICATIONS

International Search Report from corresponding international application No. PCT/US2012/057352 dated Feb. 25, 2013.

* cited by examiner

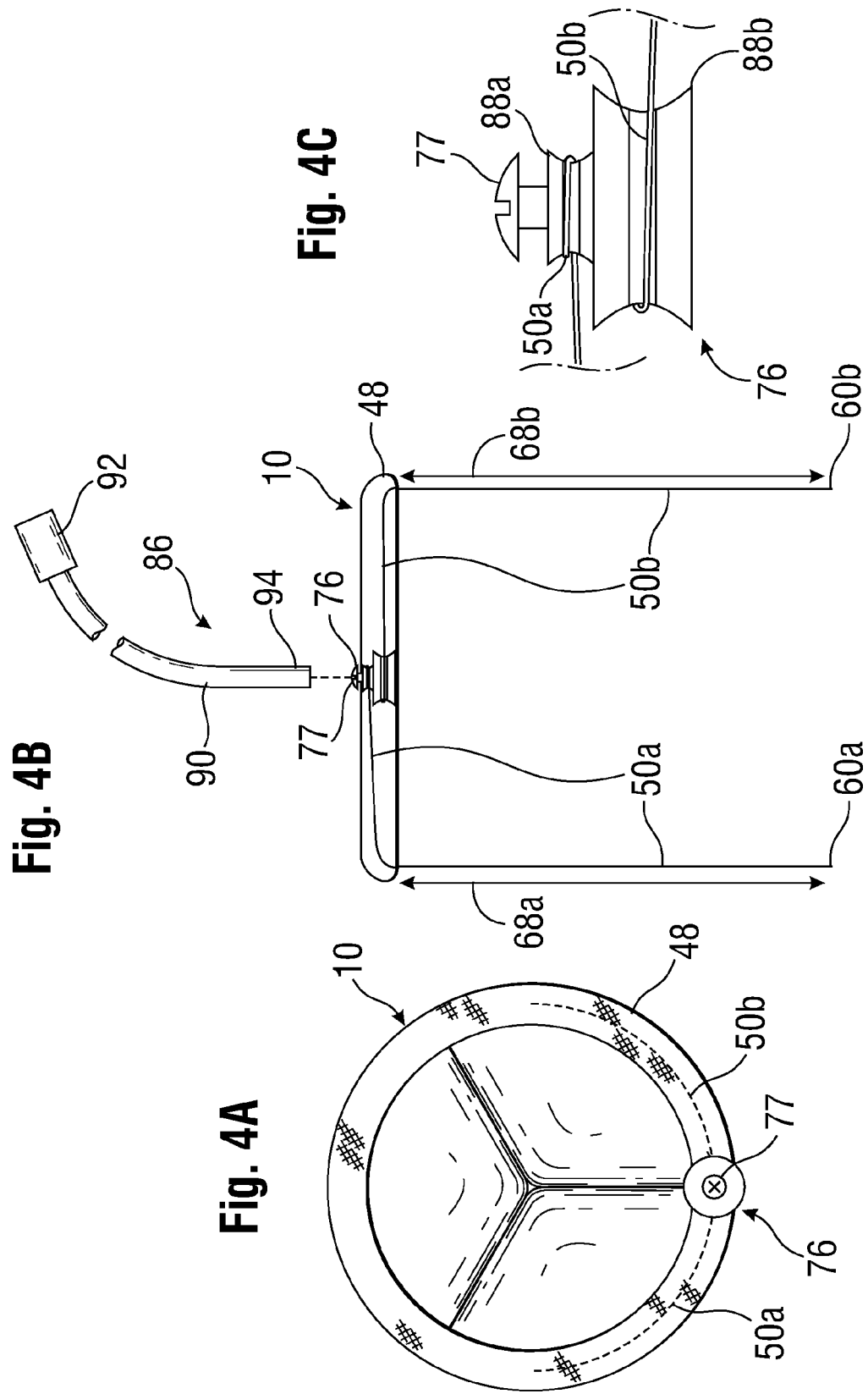

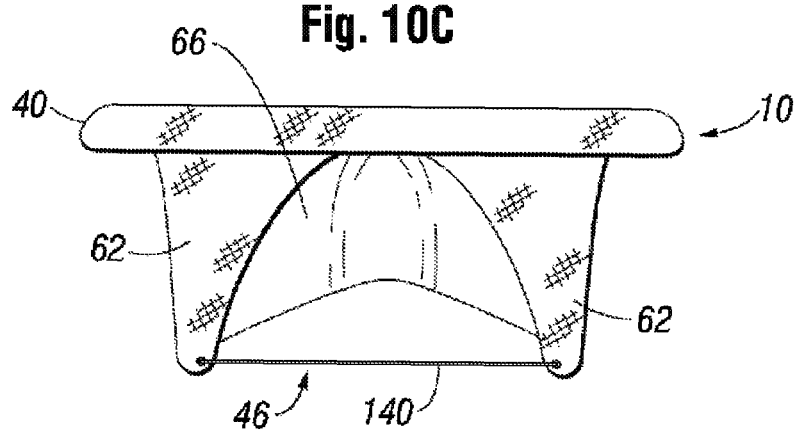
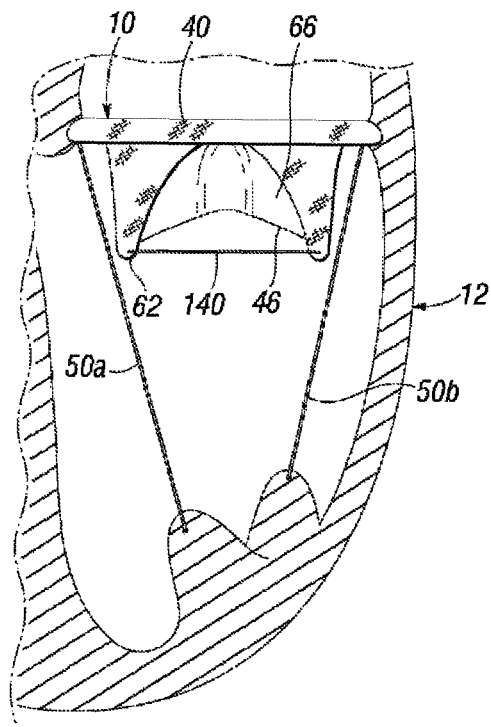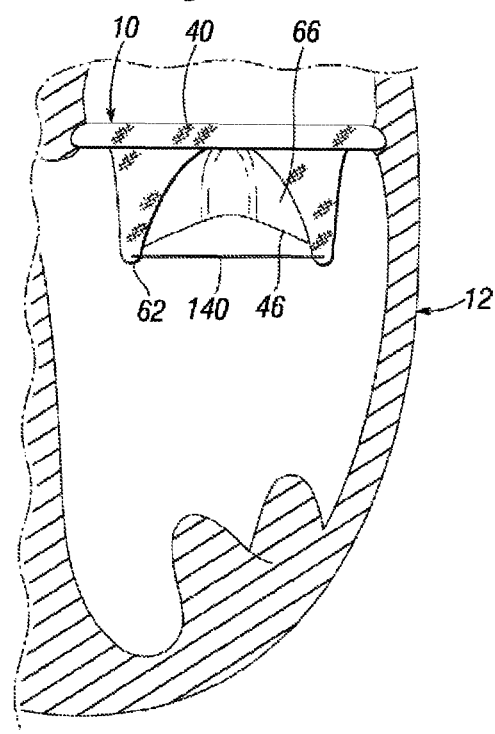

PROSTHETIC VALVE WITH VENTRICULAR TETHERS

RELATED APPLICATIONS

The present application claims priority under 35 U.S.C. §119 to U.S. Provisional Application Ser. No. 61/539,356, filed Sep. 26, 2011.

FIELD OF THE INVENTION

The current invention is directed to a prosthetic heart valve and a method for implanting such a prosthetic heart valve.

BACKGROUND OF THE INVENTION

The heart is a hollow muscular organ of a somewhat conical form; it lies between the lungs in the middle mediastinum and is enclosed in the pericardium. The heart rests obliquely in the chest behind the body of the sternum and adjoining parts of the rib cartilages, and typically projects farther into the left than into the right half of the thoracic cavity so that about one-third is situated on the right and two-thirds on the left of the median plane. The heart is subdivided by septa into right and left halves, and a constriction subdivides each half of the organ into two cavities, the upper cavity being called the atrium, the lower the ventricle. The heart therefore consists of four chambers; the right and left atria, and right and left ventricles, with one-way flow valves between respective atria and ventricles and at the outlet from the ventricles.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood or regurgitation through the valve when the leaflets are supposed to coapt together to prevent regurgitation. Valve disease can be severely debilitating and even fatal if left untreated.

As will be explained in greater detail below, the atrioventricular heart valves (i.e., the tricuspid and mitral valves) are located in the center of the heart between the atria and the ventricles of the heart, and play important roles in maintaining forward flow of blood. Atrioventricular valve dysfunction is also commonly known as "regurgitation" and affects well over one million people globally. Heart valve replacement may be indicated when there is a narrowing of a native heart valve, commonly referred to as stenosis, or when the native valve leaks or regurgitates, such as when the leaflets are calcified. When replacing the valve, the native valve may be excised and replaced with either a biologic or a mechanical valve.

Prosthetic cardiac valves have been used for many years to treat cardiac valvular disorders. The native heart valves (such as the aortic, pulmonary, tricuspid, and mitral valves) serve critical functions in assuring the forward flow of an adequate supply of blood through the cardiovascular system. These heart valves can be rendered less effective by congenital, inflammatory, infectious conditions, or other disease. Such damage to the valves can result in serious cardiovascular compromise. For many years the definitive treatment for such disorders was the surgical repair or replacement of the valve during, for example, open heart surgery.

Surgical repair of the native valve is commonly conducted using so-called annuloplasty rings. Examples of annuloplasty rings, including methods of use for repairing native valves, are disclosed in U.S. Pat. No. 4,055,861, filed Apr. 9, 1976 and entitled "Support for a Natural Heart Valve"; U.S. Pat. No. 5,041,130, filed Nov. 30, 1989 and entitled "Flexible Annuloplasty Ring and Holder"; U.S. Pat. No. 6,558,416, filed Mar. 6, 2001 and entitled "Annuloplasty Ring Delivery Method"; and in co-pending U.S. patent application Ser. No. 13/019,506, filed Feb. 2, 2011 and entitled "Devices and Methods for Treating a Heart," the entire contents of each of which are incorporated herein by reference.

In some situations, replacement of the native heart valve with a prosthetic heart valve may be the desired treatment. There are approximately 60,000 mitral valve replacements (MVR) each year and it is estimated that another 60,000 patients should receive a MVR due to increased risk of operation and age. The large majority of these replacements are accomplished through open-heart surgery, where a prosthetic heart valve is surgically implanted. Such surgically implanted prosthetic valves have a long and proven record, with high success rates and clinical improvements noted after such valve replacement. However, sometimes after implantation of a prosthetic heart valve, the heart may reshape itself in a manner which compromises the heart's function. For example, ventricular walls may already be weakened, or may become weakened, with the result that the ventricle becomes enlarged as the walls expand outward.

Although valve regurgitation often occurs due to the dilatation of the valve annulus, mitral and tricuspid valve function and competency frequently depend on the fine geometric and functional integrity of the valve's supporting structures, such as, for example, the associated subvalvular apparatus. The subvalvular apparatus of these heart valves include, among other things, the associated chordae tendinae and papillary muscles. Indeed, the underlying cause of atrioventricular valve dysfunction is sometimes considered to be a dilatation of the associated ventricular chamber (also known as ventricular remodeling), which results in displacement and tethering of the ventricle's papillary muscles. Displacement of these cardiac muscular prominences hampers correct closure of the associated atrioventricular valve during systole and causes valvular insufficiency.

Even if the dysfunctional native heart valve is replaced with a fully functional prosthetic heart valve, ventricular dilatation may already be, or may increase to be, large enough to compromise the efficiency of the pumping action of the heart. A continued progression of ventricular dilatation may end in irreversible ventricular dysfunction or congestive heart failure (CHF). CHF is a family of related conditions defined by failure of the heart to pump blood efficiently. With over one million new cases occurring each year, CHF is considered to be one of the fastest-growing cardiovascular diseases in the world. And, if left untreated, CHF may result in severe lifestyle restrictions and ultimately death. One of the causes of CHF and a very common contributor to the harmful effects of CHF is a dilatated ventricle. Another cause of CHF is Functional/Ischemic Mitral Regurgitation (FIMR). Right heart failure and functional tricuspid regurgitation (FTR) are other disease states of concern.

Thus, what are needed are methods and devices for treating ventricular remodeling and atrioventricular valve regurgitation by addressing the geometric distortion of not only the valve's annulus, but also the supporting structures of the valve.

Additionally, it would be desirable if such a technique could address ventricular remodeling and atrioventricular regurgitation in a single surgery and with a single implant, particularly in patients who are more seriously ill and could benefit most from heart valve repair, but are at greatest risk from repeated bypass.

Further, because damage to heart geometry may be progressive, initial success in reducing regurgitation via heart valve replacement may be followed by further damage to heart geometry via continued ventricular dilatation. It would therefore be desirable to employ approaches to addressing these conditions that are adjustable over time.

Accordingly, further options are needed for valve replacement, particularly for replacement of the mitral and tricuspid valves with associated ventricular treatment.

SUMMARY OF THE INVENTION

A prosthetic valve assembly and method of implanting the same is disclosed. The prosthetic valve assembly may be a prosthetic mitral valve, and includes a prosthetic valve formed by support frame and valve leaflets, with one or more tethers each having a first end secured to the support frame and the second end attached to, or configured for attachment to, papillary muscles or other ventricular tissue. The tether is configured and positioned so as to avoid contact or other interference with movement of the valve leaflets, while at the same time providing a tethering action between the support frame and the ventricular tissue. The valve leaflets may be flexible (e.g., so-called tissue or synthetic leaflets) or mechanical.

A device for treating a heart according to an embodiment of the invention comprises a prosthetic valve having a support frame and a valve portion. The valve portion may include a plurality of leaflets secured to the support frame and configured to coapt to permit blood flow in a first direction through the valve portion and to prevent blood flow in a second direction through the valve portion, wherein the first direction is opposite to the second direction, wherein the support frame comprises one or more attachment structures configured to be attached, and/or to otherwise facilitate attachment of the device, to tissue at or adjacent an annulus of a native heart valve. At least one elongate member may extend from the support frame. A distal end of the elongate member is configured to be secured to heart geometry, such as a heart wall or papillary muscle, within a ventricular chamber of the heart. The elongate member may have a usable length of between about 10 to 40 millimeters from the support frame to the distal end. An adjustment mechanism may be included for altering the usable length of the elongate member.

The prosthetic valve may be configured for surgical implantation, either via traditional open-heart or minimally invasive techniques. The support frame may have an attachment structure for securing the prosthetic valve at a desired location at a native heart valve annulus. For example, the support frame may comprise a sewing ring configured to be sutured to tissue of the annulus of the native heart valve, and/or may include other attachment structures configured to secure the support frame at the valve annulus using no (or minimal) suture, such as an expandable stent structure, clamps, skirts, or other elements configured to engage tissue of, or adjacent to, the native annulus in order to secure the prosthetic valve at the desired position. Some examples of sutureless securement devices and methods for use with the current invention are disclosed in U.S. patent application Ser. No. 12/821,628, filed Jun. 23, 2010 and entitled "Unitary Quick-Connect Prosthetic Heart Valve and Deployment System and Methods," and also in U.S. patent application Ser. No. 13/167,639, filed Jun. 23, 2011 and entitled "Systems and Methods for Rapidly Deploying Surgical Heart Valves," the entire contents of each of which are expressly incorporated herein by reference. Various methods and devices for adjusting the lengths of the elongate tether members are within the scope of the invention. The adjustment mechanism may comprise a locking mechanism configured to prevent sliding movement of the tether with respect to the support frame in at least one direction, or in both directions. The adjustment mechanism may have a component configured for rotation by a surgeon or other user, with rotation of the component adjusting the length of the tether and/or adjusting the configuration of the locking mechanism.

The tethers may pass slidingly through the support frame, with the adjustment mechanism comprising a lock configured to selectively prevent sliding movement of the elongate member with respect to the support frame. The adjustment mechanism may include a component configured for rotation. The support frame may include a hollow channel passing circumferentially through the support frame, such as through the sewing ring. The hollow channel may pass partially or completely (i.e., 360 degrees) about the circumference of the sewing ring or other support frame structure. One or more elongate members may pass within the hollow channel circumferentially at least partway or completely around its circumference.

In an exemplary version of the valve, a plurality of locking clips are embedded within the sewing ring of the heart valve through each of which passes one of the elongate tether members. The locking clips may include tubular bodies with collapsible wall structures that form the tether adjustment mechanism.

There may be one, two, three, four, or more elongate members/tethers extending from the support frame. The elongate members may extend from the support frame at different positions around the circumference thereof, and may be generally equidistantly positioned around the circumference. The tethers may be formed of a flexible metal or polymer or other suitable material.

Methods of the invention include providing a prosthetic heart valve assembly comprising a prosthetic valve, at least two anchors, and at least two tethers, wherein the prosthetic valve comprises a support frame and leaflets with the leaflets secured to the support frame to form a one-way valve structure, and wherein each tether has a proximal end secured to the support frame and a distal end secured to at least one of said anchors, wherein each tether has a tether usable length extending from the support frame to the anchor, and wherein each tether is slidingly secured to the support frame at the proximal end. The anchors are secured to ventricular tissue, such as a heart wall tissue or papillary muscle tissue within a ventricle below the native heart valve annulus. The prosthetic heart valve is advanced to the native heart valve annulus, and the support frame is secured to the annulus. Advancement and securement can be performed in an open-heart or minimally-invasive procedure. Securing the anchors to ventricular tissue may occur prior to or after securing the support frame to the native heart valve annulus. The support frame may comprise a sewing ring, and securing the support frame to the tissue of the native heart valve annulus may include suturing the sewing ring to tissue of the native heart valve annulus. The native valve annulus may be of any heart valve, with particular application to mitral and tricuspid valve.

In one embodiment, each tether has a proximal end secured to a locking clip embedded within a sewing ring of the heart valve. Preferably, a plurality of locking clips are embedded within the sewing ring of the heart valve through each of which passes one of the tethers, wherein the method including passing each of the tethers through one of the locking clips after it has been secured to ventricular tissue. Desirably, the locking clips include tubular bodies with collapsible wall structures, and the method includes providing a hollow hypotube within each of the locking clips to maintain the collapsible wall structures flexed outward, and removing the hypo tube after passing each tether through the respective locking clip.

After the support frame is secured to the native valve annulus, the tether usable length of each tether can be adjusted to a desired length, which may form the ventricle to a desired shape. With the desired usable length achieved, each tether is locked in position with respect to the support frame to prevent sliding movement thereof and to thereby fix the tether usable length at the desired length.

The method may include temporarily ceasing heart function of the heart and placing the patient on cardiopulmonary bypass, performing various steps (such as advancement and securing of the prosthetic valve to the native annulus), and then resuming heart function of the heart and removing the patient from cardiopulmonary bypass. Adjustment of the tether lengths may occur with the patient on bypass, or may occur with the patient's heart beating (e.g., after the patient is removed from bypass, with heart function restarted) and with the surgeon or other user monitoring the heart function and/or ventricular shape as the length adjustments are made.

The prosthetic valve may include an adjustment mechanism configured to adjust the usable tether length of one or more tethers, and adjusting the usable tether length may comprise rotating a component of the adjustment mechanism.

Methods of the invention may include, prior to securing the support frame to the tissue of the native heart valve annulus, removing native valve leaflets and/or subvalvular structure (e.g., chordae tendinae) from the heart.

A device according to the invention may include a brush guard assembly having one or more brush guards configured to prevent native tissue, such as subvalvular tissue (including chordae tendinae) from interacting with and/or compromising the function of the prosthetic heart valve, such as the function of the prosthetic leaflets. The brush guards may extend from and between distal portions of adjacent commissure posts of the support frame. In the case of a 3-leaflet prosthetic valve there may be 3 commissure posts with 3 brush guards forming a generally triangular fence-like structure about the outlet of the prosthetic heart valve.

The foregoing and other objects, features, and advantages of the invention will become more apparent from the following detailed description, which proceeds with reference to the accompanying figures.

BRIEF DESCRIPTION OF THE DRAWINGS

FIGS. 4A-4C are top (outflow), side (partial), and close-up views of another embodiment of a mitral valve assembly according to the invention;

FIGS. 10A-10C are perspective, bottom, and side views, respectively of a prosthetic heart valve with brush guards according to an embodiment of the invention;

FIGS. 10D and 10E are side views of embodiments of prosthetic heart valves with brush guards deployed in a heart according to an embodiment of the invention;

DETAILED DESCRIPTION OF PREFERRED EMBODIMENTS

Figure 1:
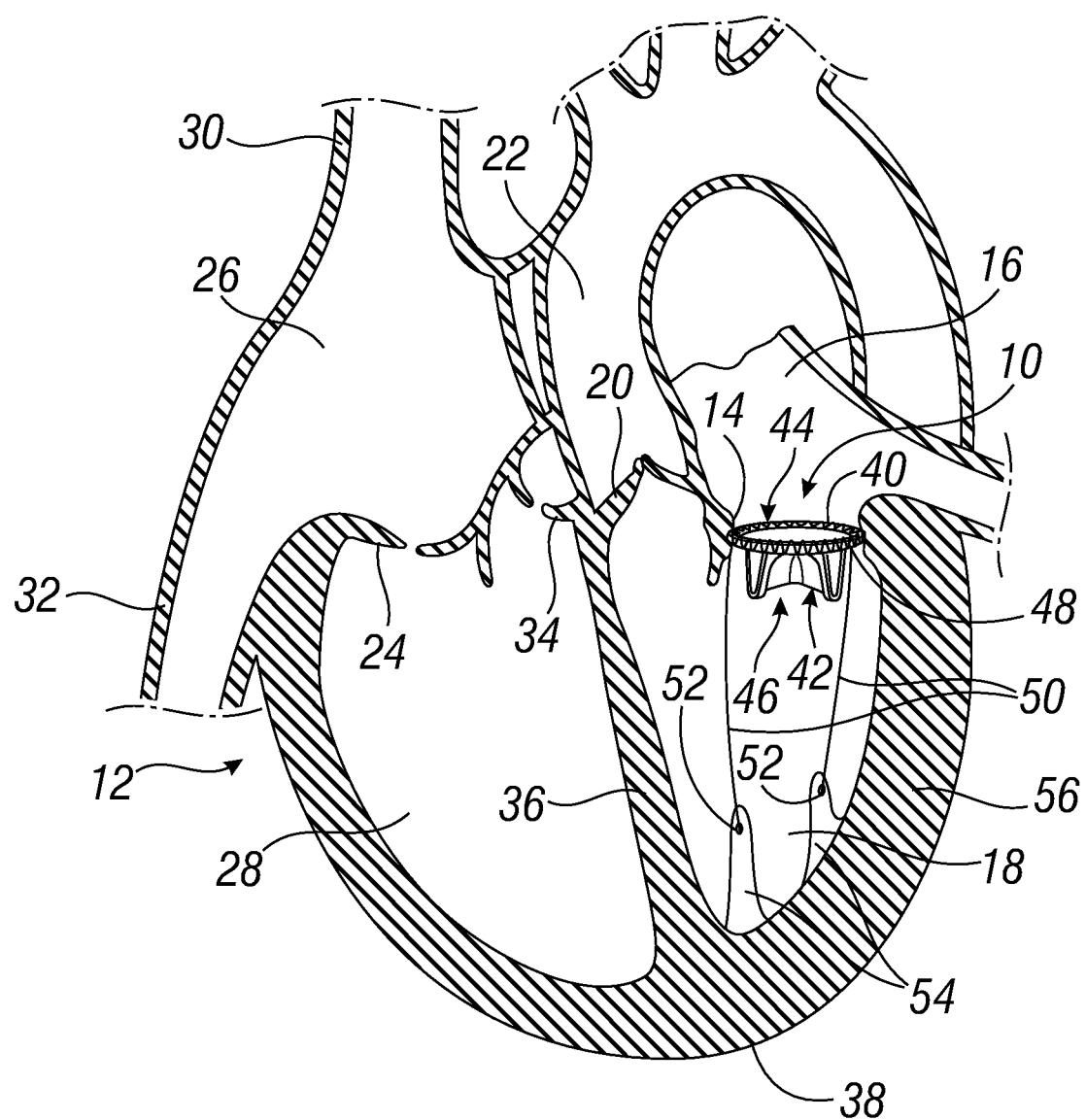
FIG. 1 shows a cross-sectional view of a heart with a prosthetic valve assembly inserted into the native mitral valve annulus with anchors in the left ventricle according to an embodiment of the invention.

FIG. 1 shows a prosthetic mitral-valve assembly 10 deployed in a human heart 12, and more specifically implanted in the native mitral valve annulus 14. Note that the native mitral valve is not depicted, as its major structures (including the native valve leaflets and native chordae tendinae) are often removed to accommodate surgical implantation of the prosthetic mitral valve assembly 10. For purposes of background, the four-chambered heart 12 is explained further. On the left side of the heart 12, the native mitral valve annulus 14 is located between the left atrium 16 and left ventricle 18. The mitral valve annulus 14 is defined as the portion of tissue surrounding the mitral valve orifice. The left atrium 16 receives oxygenated blood from the pulmonary veins. The oxygenated blood that is collected in the left atrium 16 enters the left ventricle 18 through the mitral valve.

Contraction of the left ventricle 18 forces blood through the aortic valve 20 and into the aorta 22. The aortic valve 20 is located between the left ventricle 18 and the aorta 22 to ensure that blood flows in only one direction (i.e., from the left ventricle to the aorta).

On the right side of the heart, the tricuspid valve 24 is located between the right atrium 26 and the right ventricle 28. The right atrium 26 receives blood from the superior vena cava 30 and the inferior vena cava 32. The superior vena cava 30 returns de-oxygenated blood from the upper part of the body, and the inferior vena cava 32 returns de-oxygenated blood from the lower part of the body. The right atrium 26 also receives blood from the heart muscle itself via the coronary sinus. The blood in the right atrium 26 enters into the right ventricle 28 through the tricuspid valve 24. Contraction of the right ventricle 28 forces blood through the pulmonic valve 34 and into the pulmonary arteries. The pulmonic valve 34 ensures that blood flows in only one direction from the right ventricle 28 to the pulmonary arteries.

The left and right sides of the heart are separated by a wall generally referred to as the septum 36. The portion of the septum that separates the two upper chambers (the right and left atria) of the heart is termed the atrial (or interatrial) septum, while the portion of the septum that lies between the two lower chambers (the right and left ventricles) of the heart is called the ventricular (or interventricular) septum. A healthy heart has a generally conical shape that tapers toward the apex 38.

As shown in FIG. 1, the prosthetic mitral valve assembly 10 is implanted within the native mitral valve annulus 14 to control flow through the left atrium 16 to the left ventricle 18. The prosthetic mitral valve assembly 10 depicted includes a support frame 40 with a valve portion 42 therein, and includes an inflow end 44 and an outflow end 46. In the particular embodiment depicted, the prosthetic mitral valve assembly 10 is implanted with the outflow end 46 just below the native mitral valve annulus 14. The prosthetic mitral valve assembly 10 may include a sewing ring 48 to permit the device to be sutured to the tissue of (or adjacent) the native mitral valve annulus 14 to retain the prosthetic mitral valve assembly 10 in place. As an alternative or addition to the sewing ring, the device may include other attachment structure(s) configured for sutureless (or minimal suture usage) securement to the valve annulus, such as an expandable stent structure, clamps, skirts, or other elements configured to engage tissue of, or adjacent to, the native annulus in order to secure the prosthetic valve at the desired position. Tethers 50 extend from the support frame 40 to anchors 52 secured to ventricular tissue, and more specifically (in the embodiment depicted) to the papillary muscles 54. Note that the anchors 52 could be secured to other tissue portions of the ventricular anatomy, such as to the ventricular wall 56 at various positions thereon (e.g., to the internal surface or external surface thereof). The tethers 50 may reverse, halt, and/or prevent dilatation of the left ventricle. The tethers 50 may also be used to prevent native subvalvular structures from blocking or otherwise interfering with proper operation of the valve portion (e.g., leaflets) and/or with blood flow through the valve assembly 40.

While the device is depicted in FIG. 1 as replacing the native mitral valve and reshaping the left ventricle, the apparatus and methods disclosed herein could also be used to replace the tricuspid valve and to reshape the right ventricle. In such embodiments, the device would be implanted with the support frame and valve portion secured in the native tricuspid annulus, and with the tethers secured (via, e.g., anchors) at their distal end to ventricular structures of the right ventricle.

Figure 2A:
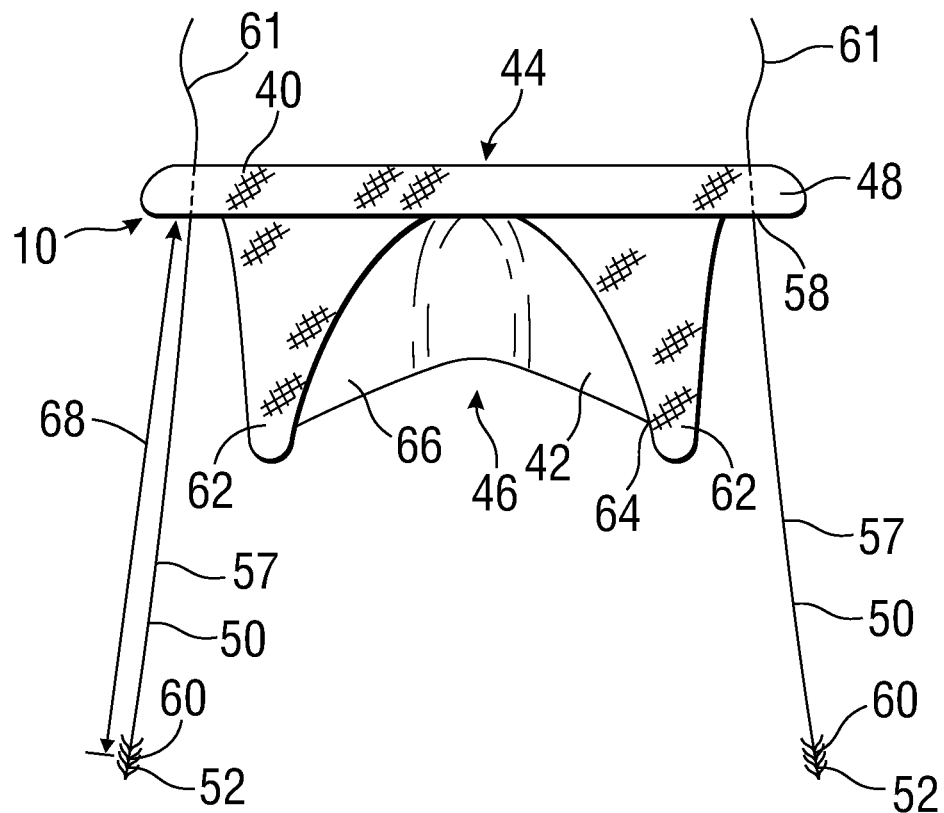
FIGS. 2A-2B are side and top (outflow) views, respectively, of an embodiment of a prosthetic mitral valve assembly according to an embodiment of the invention.
Figure 2B:
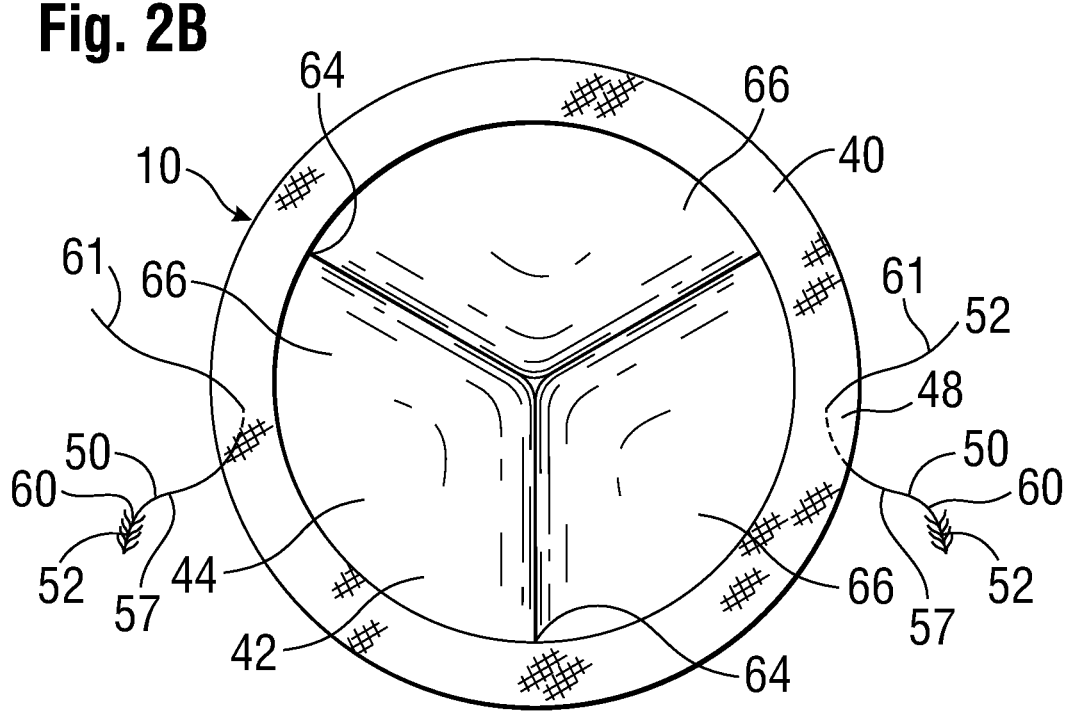

FIGS. 2A-2B depict an embodiment of a prosthetic mitral valve assembly 10 that can be implanted into a native valve annulus according to an embodiment of the invention, with tethers 50 having usable portions 57 which extend from the support frame 40 and/or sewing ring 48, with proximal ends 58 passing into (e.g., secured to, such as with a locking mechanism) the support frame 40 and having anchors 52 at their distal ends 60. Free portions 61 of the tethers 50 extend above the support frame 40 and sewing ring 48, and can be pulled by a surgeon or other user to adjust the lengths of the usable portions 57. The support frame 40 includes a sewing ring 48 and commissure posts 62, with the commissure posts 62 supporting the commissures 64 of the leaflets 66 of the valve portion 42. After the device 10 is implanted and the lengths of the usable portions 57 have been properly adjusted, the free portions 61 can be cut away from the device 10.

The support frame 40 and valve portion 42 may define a tricuspid valve assembly similar to those depicted and described in U.S. Pat. Nos. 7,871,435; 7,776,084; 6,585,766; and 6,102,944, the contents of which are expressly incorporated herein by reference.

The valve portion 42 may have a leafed-valve configuration, such as a bicuspid valve or tricuspid valve configuration. The valve portion 42 can be connected to the support frame 40 using, for example, sutures or other suitable connection techniques well-known in the art. Alternatively, the valve portion 42 can be a mechanical type valve, rather than a leafed type valve. Still further, the valve portion 42 can be made from biological matter, such as natural tissue, pericardial tissue (e.g., bovine, porcine or equine pericardium), a harvested natural valve, or other biological tissue. Alternatively, the valve portion 42 can be made from biocompatible synthetic materials (e.g., biocompatible polymers), which are well known in the art. Blood flow through the valve proceeds in a direction from the inflow end 44 to the outflow end 46. Those skilled in the art will recognize that a wide variety of valve portion designs may be used without departing from the scope of the invention.

The tethers 50 have sufficient (and preferably adjustable) "active" length 68 from the support frame 40 to the anchors 52 to permit attachment of the support frame 40 to the native valve annulus and attachment of the anchors 52 to the papillary muscles(s) or other ventricular structures while providing some tension along the tethers 50. In one embodiment of the invention, the length 68 is in the range of between about 10 to 40 mm. In the particular embodiment depicted, there are three tethers 50, and each tether 50 is secured to the support frame 40 (and more specifically to the sewing ring 48) at a position adjacent a commissure post 62. For a three-tether valve assembly such as that depicted, each tether may be secured to a different portion of the ventricular structure, or one or more tethers may share a common anchor and/or anchor point. For example, a first tether could be secured to a first one of the papillary muscles, and the second and third tethers could both be secured to the second one of the papillary muscles, either with a single (common/shared) anchor or with separate anchors implanted in that second one of the papillary muscles. Note that there could be more or fewer tethers within the scope of the invention. For example, in one embodiment, there could be just two tethers, and each could be secured to the sewing ring at a position about 180 degrees (i.e., opposite) from the other tether's position on the sewing ring. In such an embodiment, the first tether could be secured to a first papillary muscle, and the second tether could be secured to the second papillary muscle.

The tethers may be formed from material that will not biodegrade/bioresorb over time, so that the tethers will continue to provide tension to the ventricular structures to thereby prevent/treat/halt ventricular dilatation. Examples of such materials for potential use with the invention include self-tensioning textiles or alloys. Textiles could include monofilament or multi-filament, including PTFEs, polyesters, nylons, and others. Alloys could include nitinol, CoCr, stainless steel alloys, and others. The tethers may preferably be formed from materials which are substantially non-elastic, and/or which have sufficient elasticity to permit stretching to accommodate ventricular structural movements as the heart beats. For example, where the tethers are anchored to the papillary muscles, substantially non-elastic tethers may be used, with the papillary muscles themselves providing sufficient elasticity to accommodate movement of the ventricular structure during heart beats. Where tethers are anchored to the ventricular wall itself, some sort of elastic structure may be required, either on the tethers and/or the anchors, to accommodate movement of the ventricular wall during heart beats.

Figure 3A:
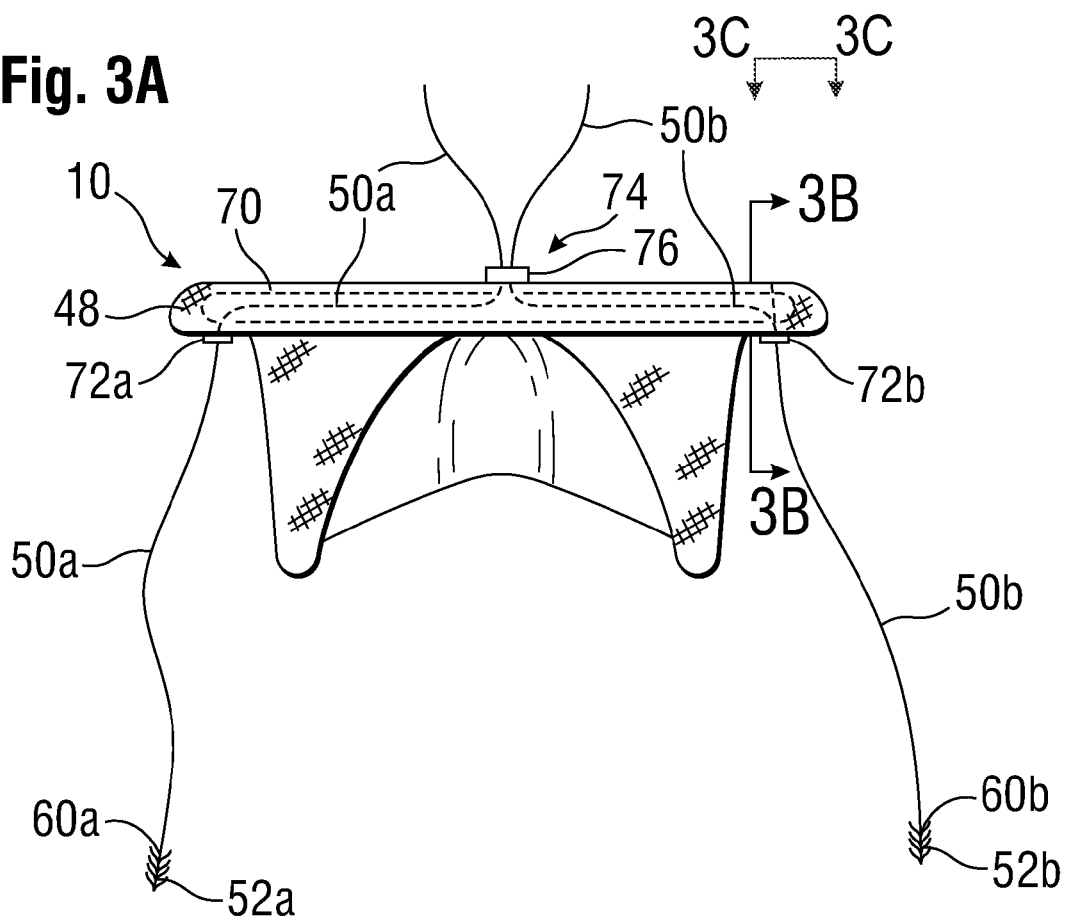
FIG. 3A-3C are side, cross-sectional (close-up), and top (close-up) views of an embodiment of a prosthetic valve assembly according to an embodiment of the invention.
Figure 3B:
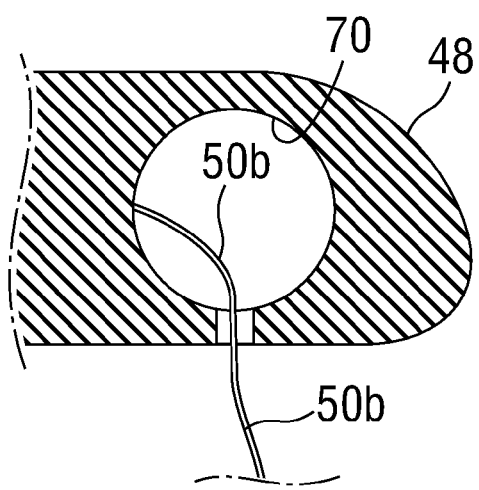
Figure 3C:
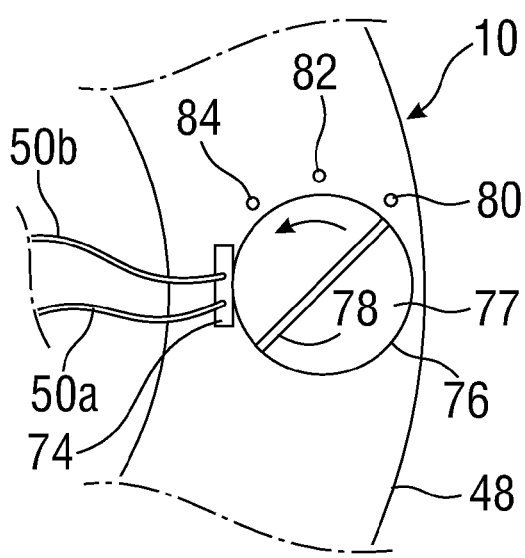

FIGS. 3A-3C depict a prosthetic mitral valve assembly 10 according to an embodiment of the invention. The assembly 10 includes two tethers 50a, 50b, each with a separate anchor 52a, 52b at its distal end 60a, 60b. The device 10 includes a hollow channel 70 within, and (in the particular embodiment depicted) passing entirely around (i.e., 360 degrees) the circumference of the sewing ring 48. The tethers 50a, 50b enter the sewing ring 48 and hollow channel 70 via lower openings 72a, 72b, which in the embodiment depicted are about 180 degrees apart around the circumference of the sewing ring 48. The tethers 50a, 50b pass through the hollow channel (which may include one or both tethers passing partially and/or entirely around the hollow channel) and exit from a single top opening 74. A locking mechanism 76 can be used to selectively lock the tethers 50a, 50b in position. Note that separate top openings and/or separate locking mechanisms for tethers are also within the scope of the invention.

Locking mechanisms for use with the invention may be able to be switched between one or more configurations. In the particular embodiment depicted in FIG. 3C (which is a close-up top view of the locking mechanism 76), the locking mechanism 76 includes a rotational control 77 with a rotational marker 78, such as a slit configured to receive a screwdriver, etc., which may be rotated by a surgeon or other user by using a screwdriver or similar flat-edge device such as a scalpel to engage the slit and rotate the control 77. The locking mechanism can thus be transformed from: an open configuration (with control 78 rotated to align with position marker 80, which is the position depicted in FIG. 3C) in which the tether(s) is free to move proximally and distally with respect to the locking mechanism 76 and sewing ring 48; and/or a one-way position (with control 78 rotated to align with position marker 82) in which the tether(s) may be slid proximally (i.e., upward with respect to valve device) to reduce the tether length below the device (i.e., the length within the ventricle); and/or a locked position (with control 78 rotated to align with position marker 84) in which the tether(s) cannot move either distally or proximally with respect to the locking mechanism. The locking mechanism may be secured to the device at various positions. In one embodiment, the locking mechanism is positioned within the sewing ring itself.

FIGS. 4A-4C depict an embodiment of a locking mechanism 76 and lock actuating tool 86 for use with a device 10 according to an embodiment of the invention. The locking mechanism 76 may include a control 77 and pulleys 88a, 88b about which tethers 50a, 50b are wrapped. Tethers 50a, 50b may be secured to and terminate at the pulleys 88a, 88b, as depicted, or may have free ends extending away from pulleys and above the device 10 which a surgeon or other user can pull upon to assist in pulley rotation. The pulleys 88a, 88b can be rotated, either together or individually (depending on the particular lock design) to synch the tethers 50a, 50b to adjust their usable lengths 68a, 68b. Actuating tool 86 may be any device suitable for activating locking mechanism and/or causing rotation of pulleys 88a, 88b. As shown in FIG. 4B, actuating tool 86 may include a shaft 90, a proximal end 92 (which may include a handle for grasping and rotation by the user), and a distal end 94. Shaft 90 may include any geometric configuration and/or dimensions suitable for advancing actuating tool distal end 94 to device 10 within a patient's heart. For example, shaft 90 may include a length that is sufficient to traverse a patient's vasculature so as to be advanced into a patient's heart from outside of the patient's body.

In embodiments where locking mechanism(s) 76 is a screw or other similarly keyed component, distal end 94 of actuating tool 86 may include one or more geometric configurations configured to mate with corresponding geometric configurations on locking mechanism, such that rotation of actuating tool 86 results in corresponding rotation of the locking mechanism control 77 to which the distal end 94 is mated. As depicted most clearly in FIG. 4C, in the particular embodiment depicted the pulleys 88a, 88b are secured to each other so that they rotate at the same rate, but the upper pulley 88a has a smaller diameter than the lower pulley 88b, so that rotation of the locking mechanism 76 causes more tightening of tether 50b than of tether 50a. Note that the pulleys 88a, 88b may alternatively have the same diameter, and/or be separably rotatable, and/or be part of entirely separate locking mechanisms, e.g., positioned about the periphery of the device 10.

In some embodiments, one or more of locking mechanisms 76, 76b and/or actuating tool 86 may be provided with a feature for providing feedback to an operator. Such feedback may communicate to an operator, for example, the amount of adjustment made to the usable lengths 68a, 68b of tethers 50a, 50b. In accordance with one embodiment of the present disclosure, such feedback may be tactile. For example, it is contemplated that as an operator is adjusting one or more aspects of device 10, the operator may experience a series of resistances, wherein each resistance corresponds to a predetermined quantity of adjustment, such as, for example, one (1) millimeter. In other embodiments, the feedback provided to an operator may be audible, such as a "click", and/or visual.

Figure 5:
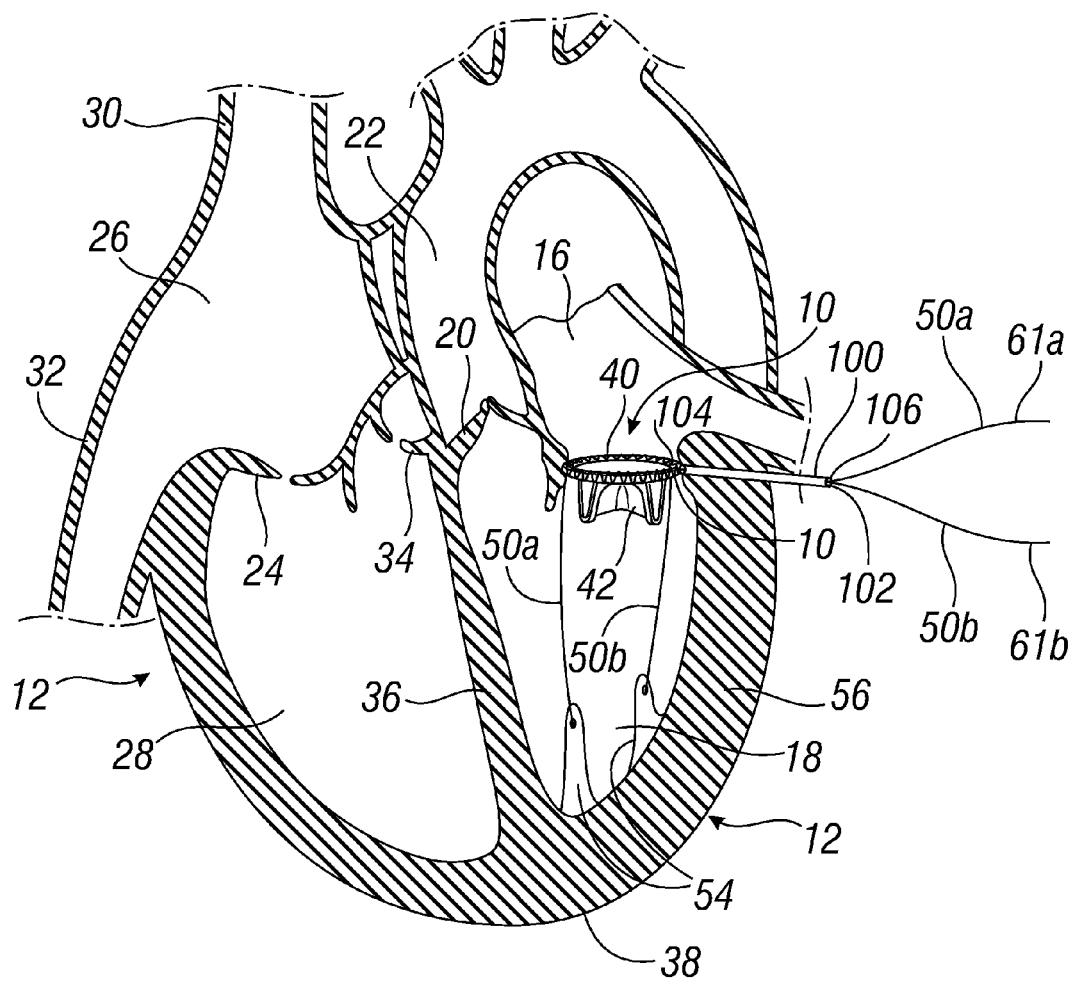
FIG. 5 is a cross-sectional view of a heart with a prosthetic valve assembly inserted into the native mitral valve annulus with anchors to papillary muscle tips in the left ventricle according to an embodiment of the invention.

In some embodiments, such as that depicted in FIG. 5, device 10 may include one or more extension shafts 100 extending away from support frame 40 and out of the patient's heart (and may extend all the way out of the patient's body). An extension shaft 100 may include a lumen 102 within which free portions 61a, 61b of one or more tethers 50a, 50b extend from support frame 40 from the distal end 104 of the extension shaft 100 and continue through the shaft to a proximal end 106 positioned outside of the patient's heart (and possibly outside of the patient's body), so as to enable adjustment of device 10 without requiring direct access to within the patient's heart or patient's body. (Note that for the shaft 100, the terms distal and proximal are indicated with respect to a surgeon or other user accessing the device from outside the heart.) Tethers 50a, 50b, individually or collectively, may be pulled and secured in place from outside of a patient's heart and/or body to effect the adjustments described above. The extension shaft 100 may be rigid or flexible, and may be attachable and/or detachable from support frame 40 at the shaft distal end 104 as desired. In one embodiment, the extension shaft 100 may extend from the distal end 104 secured to the support frame 40 to a proximal end 106 positioned in a subcutaneous pocket (not shown), allowing relatively easy access for a surgeon or other user to adjust tethers 50a, 50b extending to and/or out of the proximal end 106.

Figure 6:
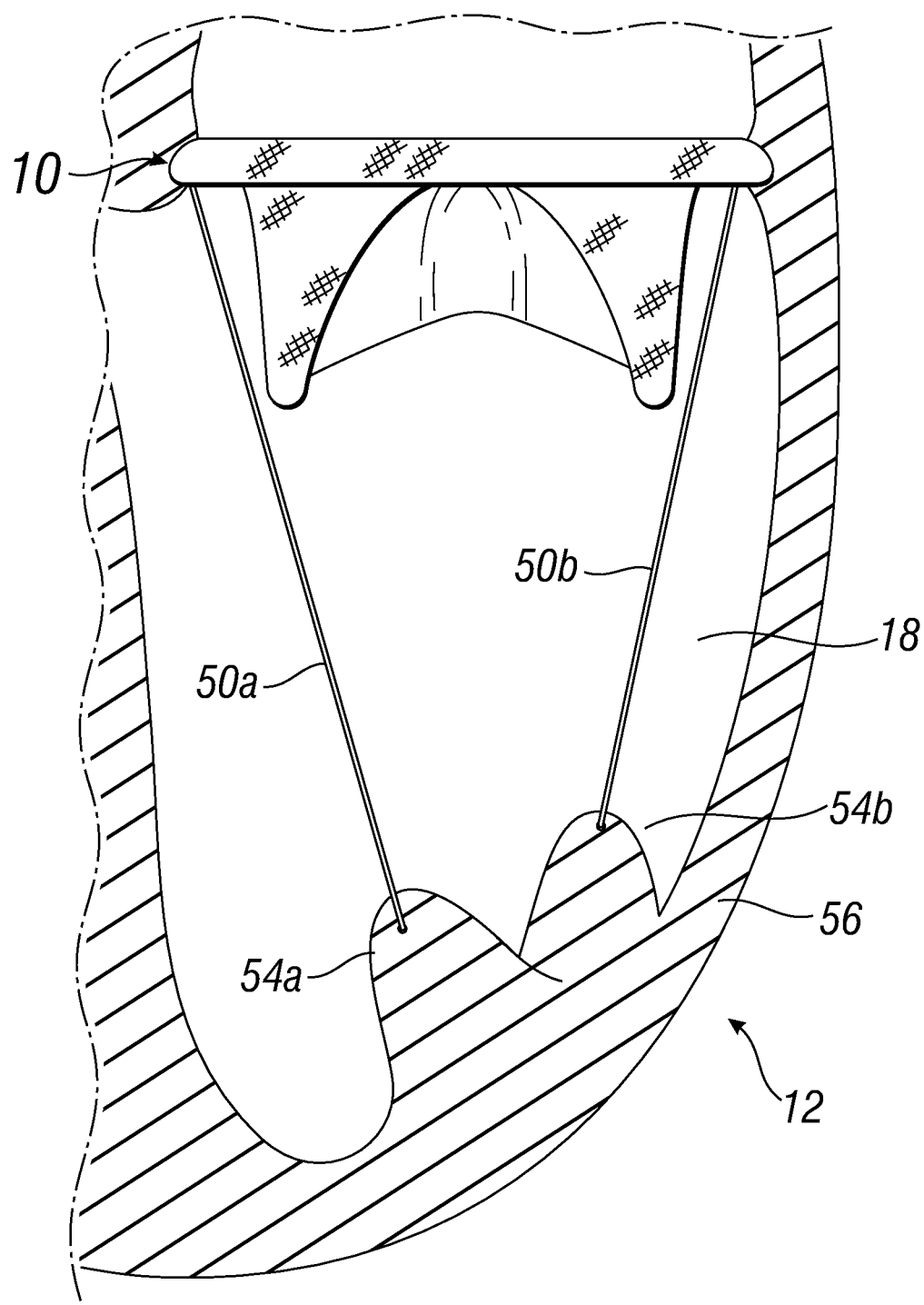
FIG. 6 is a cross-sectional view of a heart ventricle with a prosthetic heart valve with anchors secured to papillary muscles according to an embodiment of the invention.

As briefly noted above, tether distal ends may be secured (e.g., via anchors) to heart structure, such as, for example, a papillary muscle and/or a heart wall. As shown in, for example, FIG. 6, one tether 50a may be secured to an anterior papillary muscle 54a of the left ventricle 18, and another tether 50b may be secured to a posterior papillary muscle 54b of the left ventricle 18. Although not depicted, those of ordinary skill in the art will readily recognize that, in at least some embodiments, tethers may traverse the ventricle so that tether

50a may be secured to a posterior papillary muscle 54b or heart wall structure and tether 50b may be secured to an anterior papillary muscle 54a or heart wall structure. Furthermore, the principles of the present disclosure also contemplate a single tether extending from the device, extending through one of the anterior papillary muscle and the posterior papillary muscle, and then passing across the lower ventricular portion and being secured to the other of the anterior papillary muscle and the posterior papillary muscle. In such embodiments, pulling on the single tether may alter the positioning of both papillary muscles.

Figure 7:
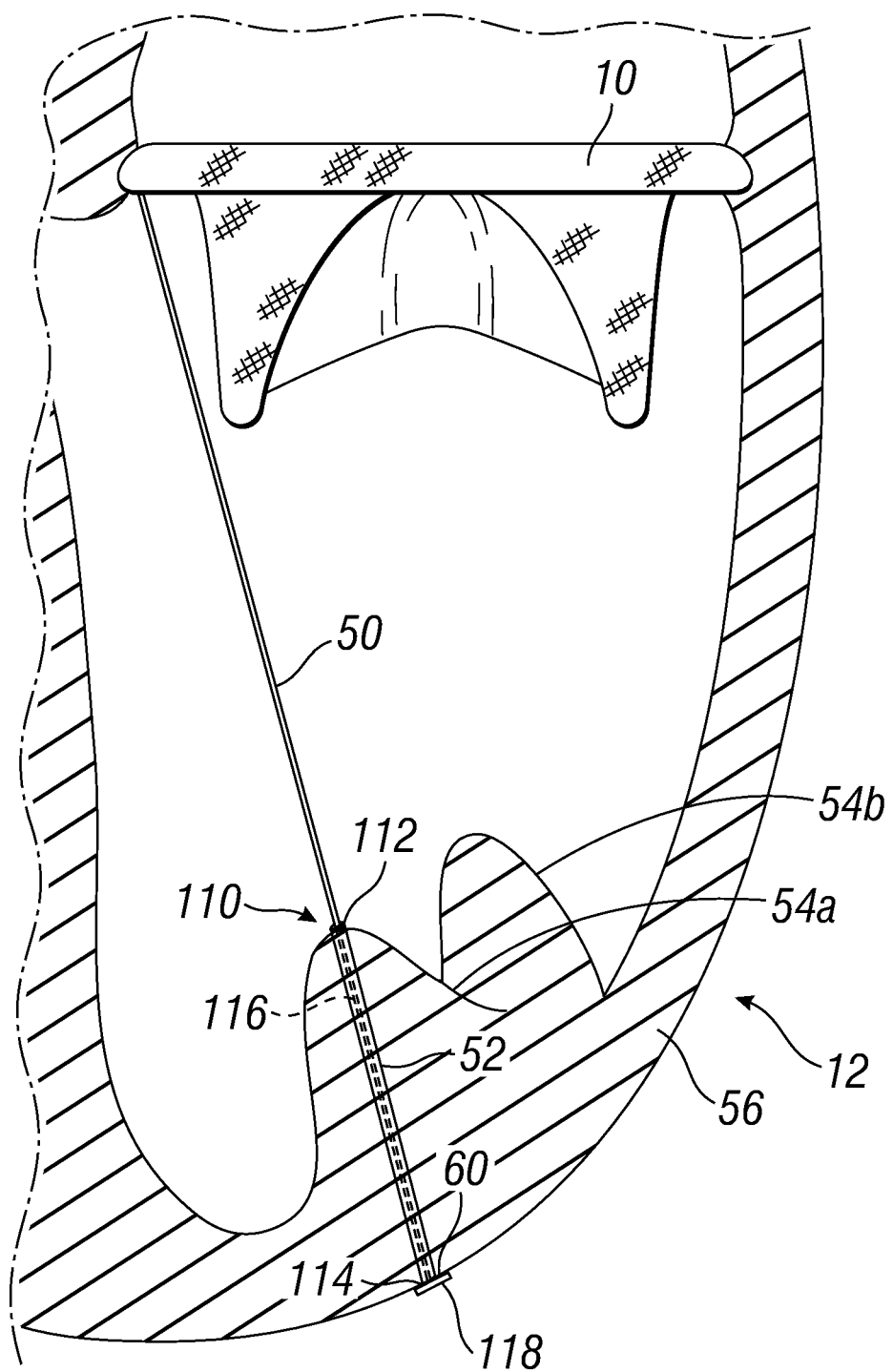
FIG. 7 is a cross-sectional view of a heart ventricle with a prosthetic heart valve with a single anchor secured through a papillary muscle to a location outside the heart according to further embodiment of the invention.

As alluded to above, distal ends of tethers may be secured to papillary muscles of a ventricle, or may be secured transmurally to a heart wall, such as, for example, an external surface of ventricle wall 56, as shown in FIG. 7, or an internal surface thereof (not shown). In embodiments where a distal end 60 of a tether 50 is secured to an external surface of the ventricular heart wall 56, the device 10 may further include one or more anchors 52 in the form of a tubular member 110 for providing a channel through heart structure, such as, for example, a papillary muscle 54a, 54b and/or a ventricle wall 56. The tubular member 110 may be configured to minimize the wear on heart structure caused by relative movement of tether(s) 50 and the heart structure (e.g., papillary muscle 54 and/or ventricle wall 56) to which it is secured.

Tubular member 110 may include any suitable geometric configuration and dimensions. For example, tubular member 110 may be substantially cylindrical in shape. Tubular member 110 may be made of any suitable biocompatible materials, including, but not limited to, stainless steel. As shown in FIG. 7, tubular member 110 may include a first opening 112, a second opening 114, and a lumen 116 extending therebetween. Lumen 116 may be configured to receive one or more tethers 50 therein. In some embodiments, the inner surfaces of lumen 116 may be coated with, for example, a hydrophilic coating to facilitate relative movement between the elongate member received and tubular member 110. In embodiments where tethers 50 may be secured to a ventricular wall 56 with an anchoring member, such as, for example, anchor pad 118, the anchoring pad 118 or other anchoring member may be formed integrally with tubular member 110.

Note that an anchor used with the invention may be configured to effectuate adjustment of the tether length, such as by having an anchor having an adjustable support pad (e.g., with a spool or pulley about which the tether can be synched) to permit the tether usable length to be adjusted from outside the heart. Such adjustable support pads and methods of their use are depicted and discussed in U.S. Pat. No. 7,871,368, entitled "Apparatus, System, and Method for Applying and Adjusting a Tensioning Element to a Hollow Body Organ," the entire contents of which are hereby incorporated herein by reference.

Figure 8A:
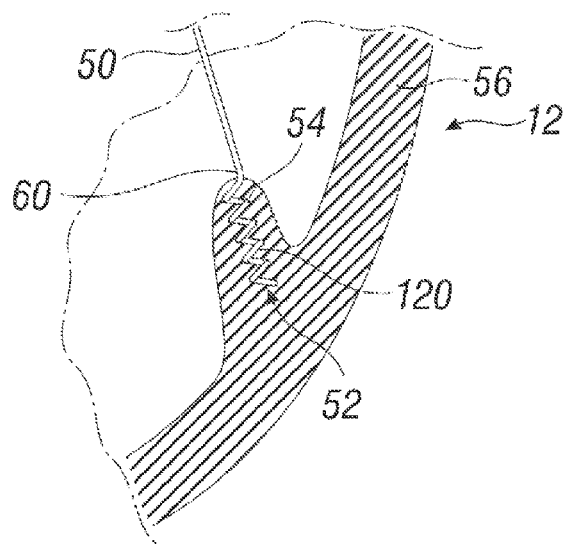
FIGS. 8A-8D are cross-sectional views of a heart ventricle with various anchors according to embodiments of the invention.
Figure 8B:
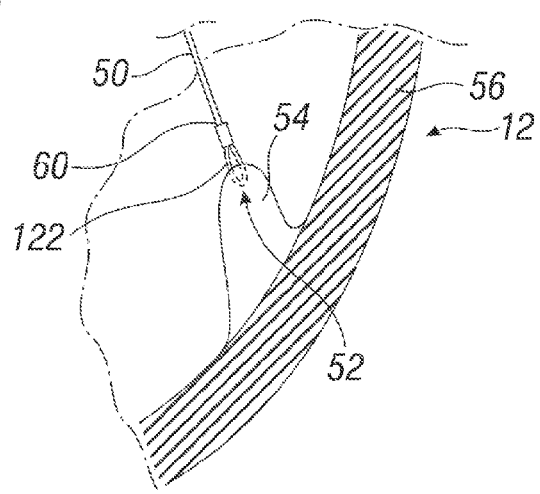
Figure 8C:
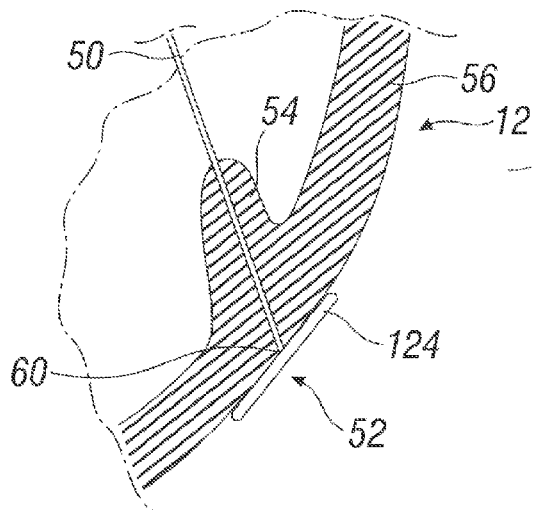
Figure 8D:
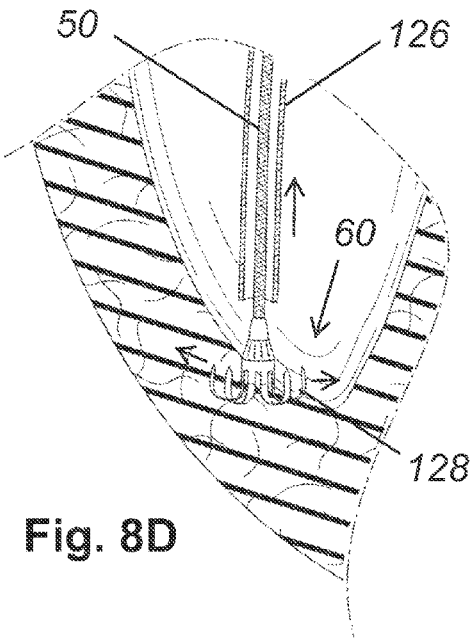

As noted above, tether distal ends may be configured to be secured (directly or via anchors, etc.) to heart structure, including, but not limited to, a papillary muscle or a heart wall. Tether distal ends may be secured to heart structure by any suitable manner known in the art that may be configured to allow forces acting on tethers to pull the heart structure inwards laterally or vertically. In one embodiment, for example, FIG. 8A depicts an anchor 52 formed as a screw 120, which may be configured to penetrate heart tissue (e.g., a papillary muscle or heart wall) to anchor the tether distal end 60 to heart tissue. In the exemplary embodiment depicted in FIG. 8B, tether distal end 60 may include a loop 122 configured to be sewn through heart structures, such as, for example, the depicted papillary muscle, with the loop 122 acting as the anchor to the heart tissue. In the exemplary embodiment depicted in FIG. 8C, tether distal end 60 may be configured to extend transmurally to an exemplary anchor 52 in the form of a support pad 124. Those of ordinary skill in the art will readily recognize that distal end 60 of tether 50 may be sewn to pad 124 or otherwise mechanically connected thereto, such as via the techniques and devices depicted and described in U.S. Pat. No. 7,871,368. In addition, the principles of the present disclosure contemplate embodiments where anchor and tether distal end are made of a one-piece construction, which would obviate the need to connect tether distal end to anchor. Finally, FIG. 8D shows a further anchoring technique wherein distal end 60 of tether 50 has a series of curled fingers or barbs 126 that deploy outward from a straightened configuration when expelled from a delivery tube 128. The distal end 60 thus resembles a grappling hook when deployed, and is shown anchored within the ventricular wall as opposed to one of the papillary muscles, though either anchoring site is contemplated.

Anchors and their associated structures may have any suitable geometric configuration and dimension known in the art. In addition, anchors may be fabricated from any suitable biocompatible material known in the art. In some embodiments, the anchors may include any suitable covering or coating known in the art. For example, anchors may include a fabric covering configured to promote tissue ingrowth.

As discussed to above, the devices and methods described herein may be applicable to any of the four valves within a patient's heart. Although the embodiments disclosed herein have been discussed relative to a mitral valve of a heart, those of ordinary skill in the art will readily recognize that the principles of the present disclosure may be equally applicable to, for example, a tricuspid valve.

Figure 9:
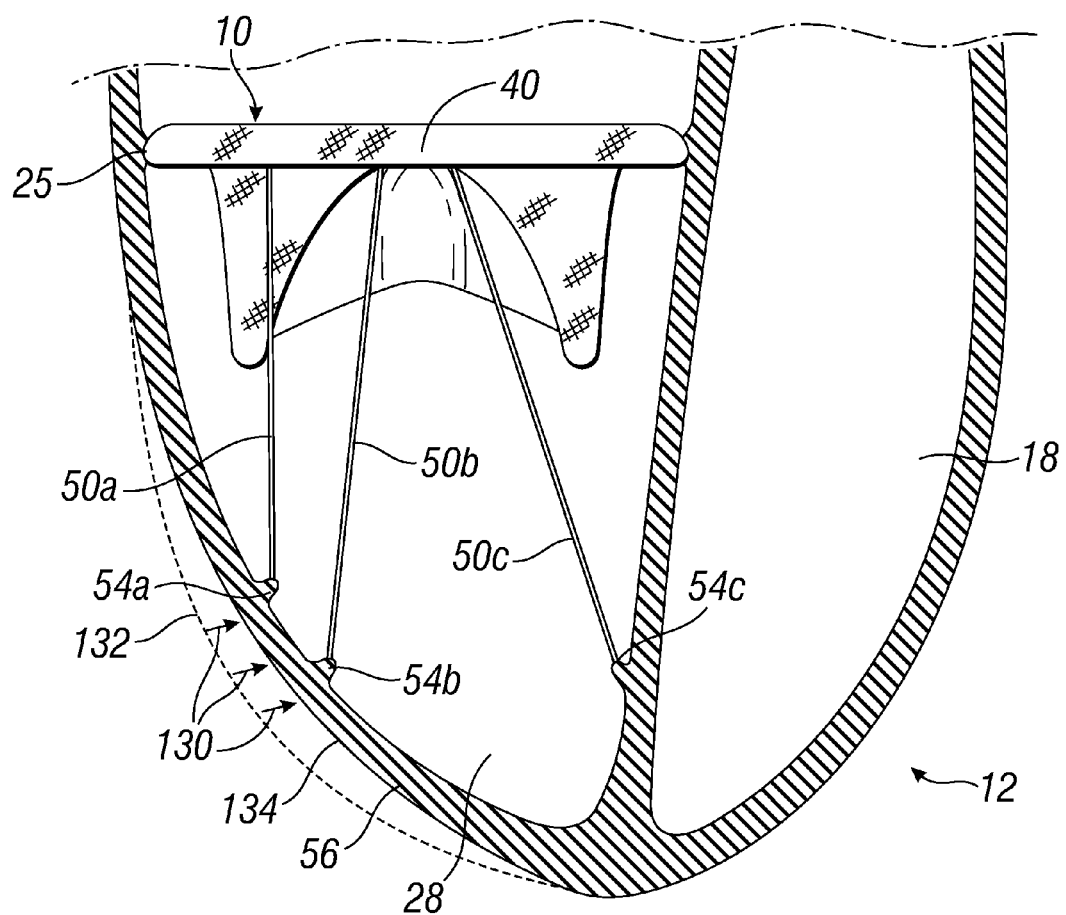
FIG. 9 is a cross-sectional view of a heart with a prosthetic valve assembly inserted into the native tricuspid valve annulus with tethers anchored in the right ventricle according to an embodiment of the invention.

FIG. 9 depicts a device 10 of the invention implanted in a tricuspid valve annulus 25 with tethers 50 extending into the right ventricle 28 of the heart 12 in accordance with the principles of the present invention. Device 10 may include at least three tethers 50a, 50b, 50c extending from support frame 40 for connection to heart structure, including, but not limited to, a heart wall 56 or papillary muscles 54 associated with right ventricle 28. The particular embodiment depicted includes tethers 50a, 50b, 50c secured to the papillary muscles (e.g., posterior papillary muscle 54a, anterior papillary muscle 54b, and septal papillary muscle 54c) of the right ventricle 28. Those of ordinary skill in the art will readily recognize that one or more of tethers 50a, 50b, 50c may be secured to the heart wall 56, as discussed in connection with the use of devices in the left ventricle as discussed elsewhere in this application. Furthermore, the length of one, two, or all of tethers 50a, 50b, 50c device 10 may be adjustable to, among other things, alter the shape or dimension of the heart structure connected to tethers 50a, 50b, 50c. Indeed, as indicated by arrows 130, device 10 may be configured to draw a heart wall 56 inwards from the position indicated by dashed line 132 to the position indicated by solid line 134.

Figure 10A:
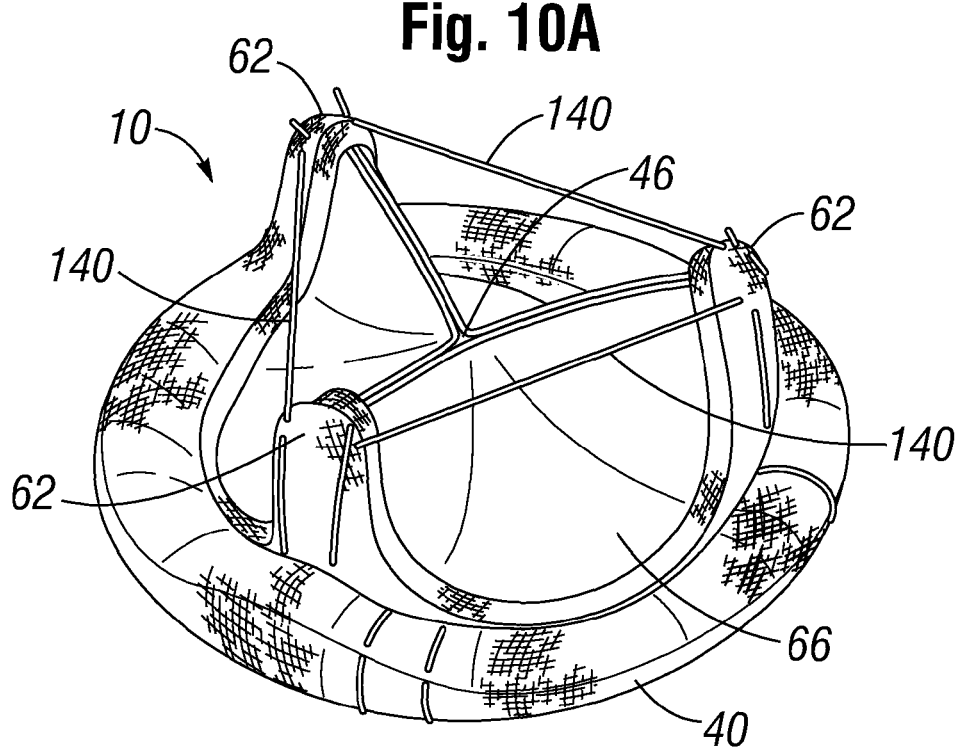
Figure 10B:
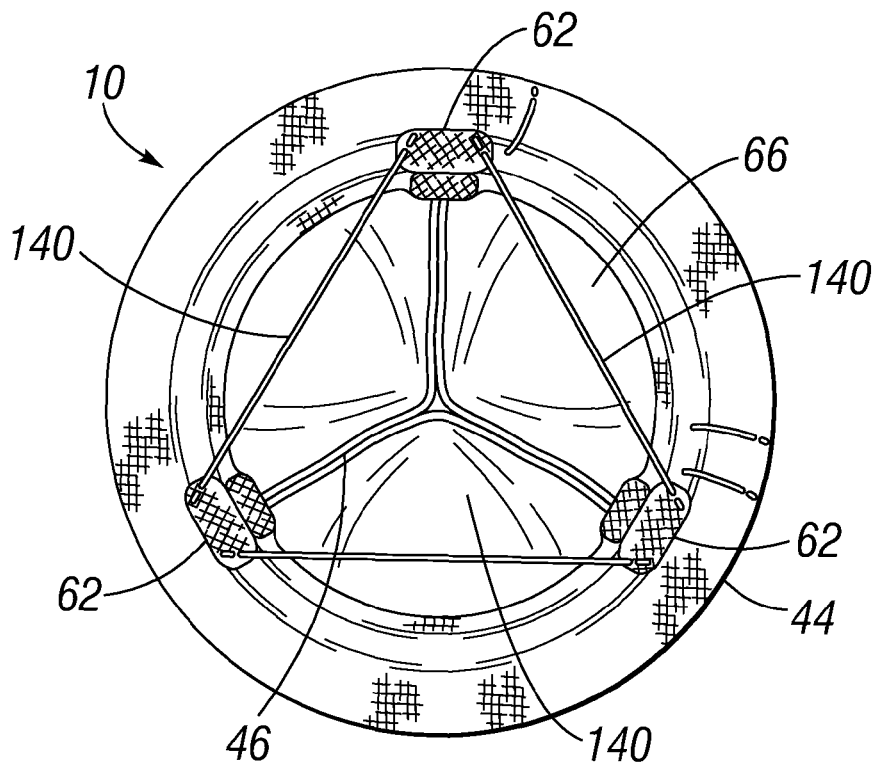

FIGS. 10A-10C depict a prosthetic valve assembly 10 having brush guards 140 extending from and between the commissure posts 62 of the support frame 40. The brush guards 140 may extend from a position toward the distal end of each commissure post 62, and may be positioned just radially outside of the extreme "open" positions of the leaflets to prevent the leaflets 66 from contacting the brush guards 140. The brush guards 140 create a triangular fence-like enclosure about the prosthetic valve leaflets 66, and serve to prevent native subvalvular structures from blocking or otherwise interfering with the leaflets 66 and/or outflow 46 of the prosthetic valve assembly 10. The brush guards 140 and tethers, alone or together, can create a protective area around the prosthetic valve outflow 46 so that the native subvalvular structures cannot interfere with the prosthetic valve operation. In an embodiment such as that depicted in FIGS. 10A-10C, the brush guards 140 are positioned at or near the distal ends of the commissure posts 62, with a large opening between each brush guard 140 and the base of the support frame 40 which permits blood to flow freely and unobstructed therethrough and to/from the valve leaflets 66. Note that the brush guards 140 may be used on a prosthetic heart valve in combination with tethers such as those disclosed in the current application, as depicted in FIG. 10D, or can be used without such tethers, as depicted in FIG. 10E.

The brush guards may be formed from material similar to, or identical to, the materials of the tethers, such as using common suture materials such as nylon, polypropylene, polyester, etc. The brush guards may be made out of metal (e.g., nitinol, cobalt chromium, stainless steel, etc.), and may form a rigid triangle to protect the leaflets. The brush guards may be flexible (which may be under tension) or rigid, and may be padded or otherwise shaped (e.g., with smooth rounded surfaces) to protect native tissue that might come into contact with the brush guards.

Figure 11A:
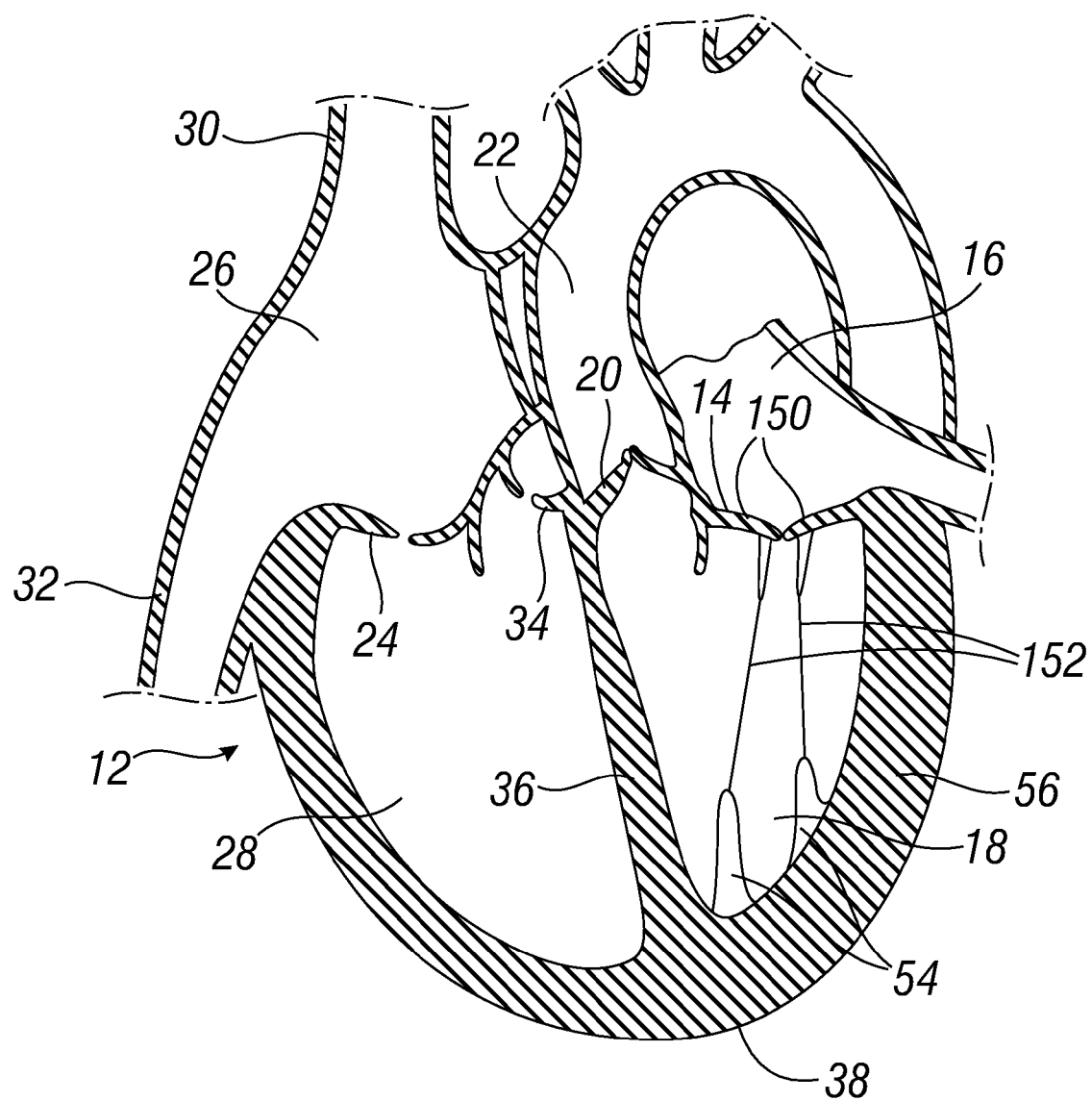
FIGS. 11A-11E are cross-sectional views of a heart having a prosthetic valve assembly mounted in the mitral valve annulus with tethers and anchors secured within the left ventricle.
Figure 11B:
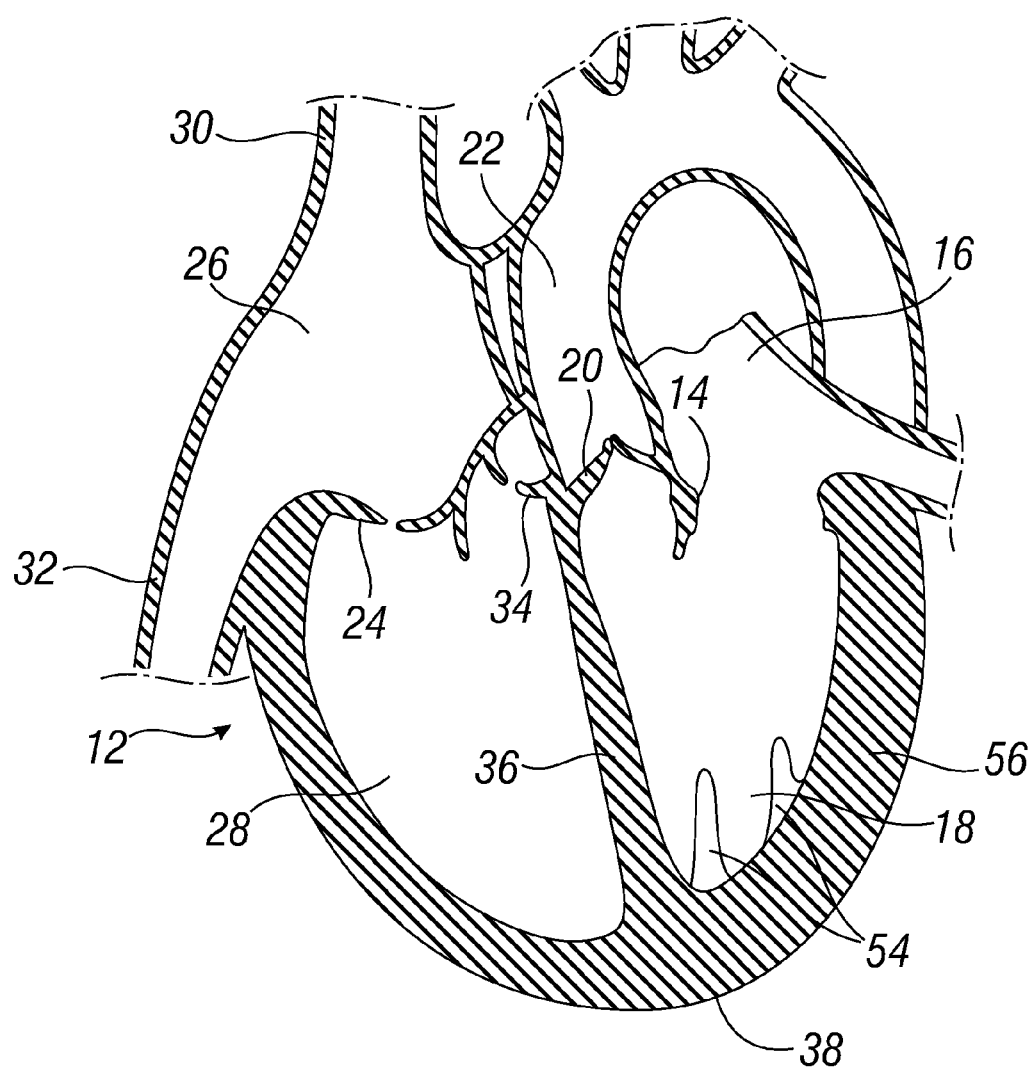

FIGS. 11A-11E depict an exemplary method of implanting a device 10 according to the invention. FIG. 11A depicts the heart 12 with all native valve structures intact, including the native mitral valve leaflets 150 and native chordae tendinae 152 prior to the implantation process. As depicted in FIG. 11B, the native mitral valve leaflets and native chordae tendinae are removed, either surgically (e.g., open heart) or via minimally-invasive and/or percutaneous techniques. Note that removal of the native mitral valve leaflets and/or native chordae tendinae is optional, depending on the particular application.

Figure 11C:
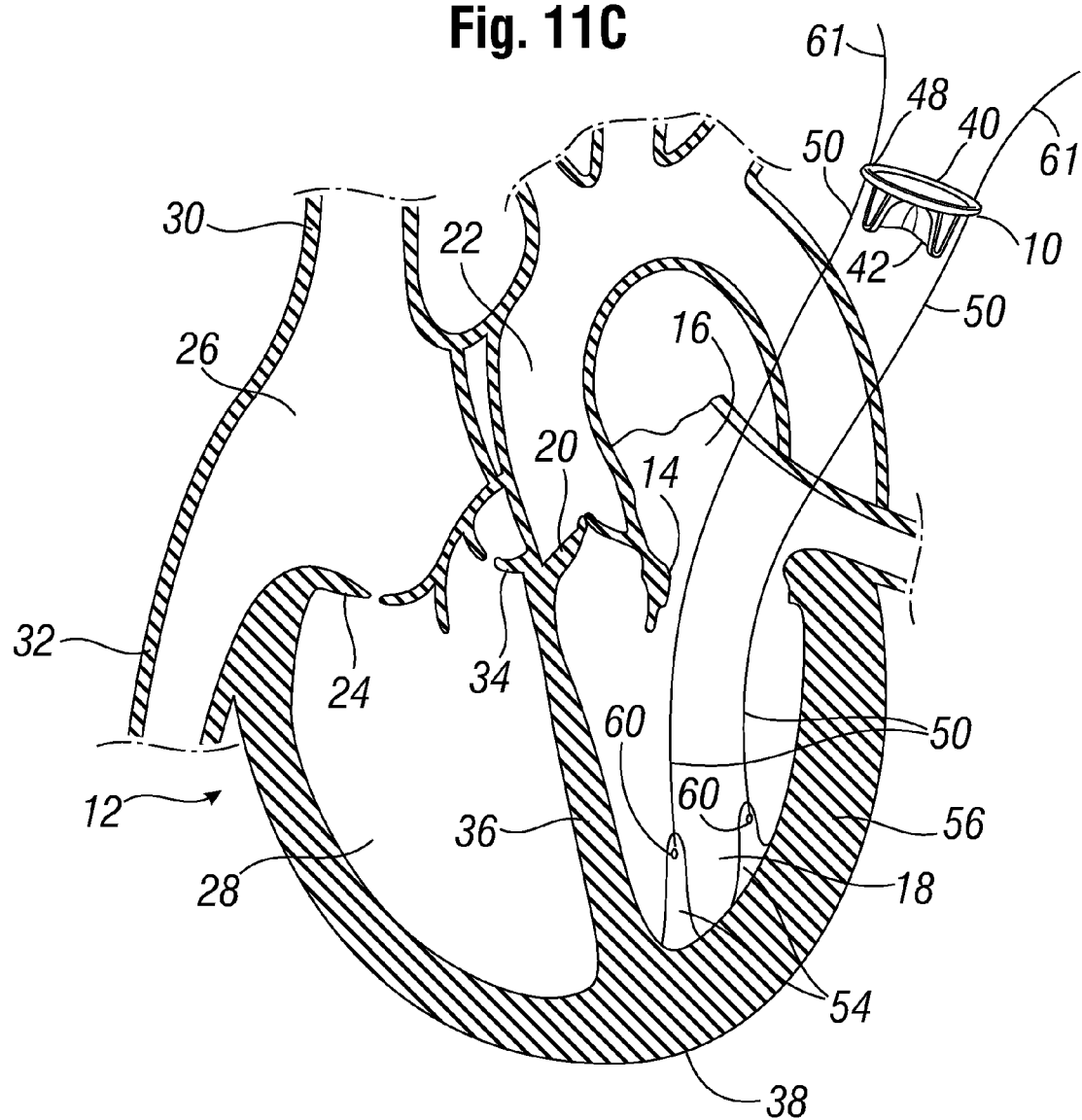

As depicted in FIG. 11C, distal ends 60 of tethers 50 are secured to the papillary muscles 54. The free ends 61 of tethers 50 are then passed through the support frame 40, such as by being threaded through the sewing ring 48 (e.g., through an optional hollow channel) and/or any applicable locking mechanism. Note that the tethers may have been previously passed through the support frame and/or locking mechanism, either by a user at the beginning of/prior to the procedure or by the manufacturer during production of the prosthetic heart valve assembly.

Figure 11D:
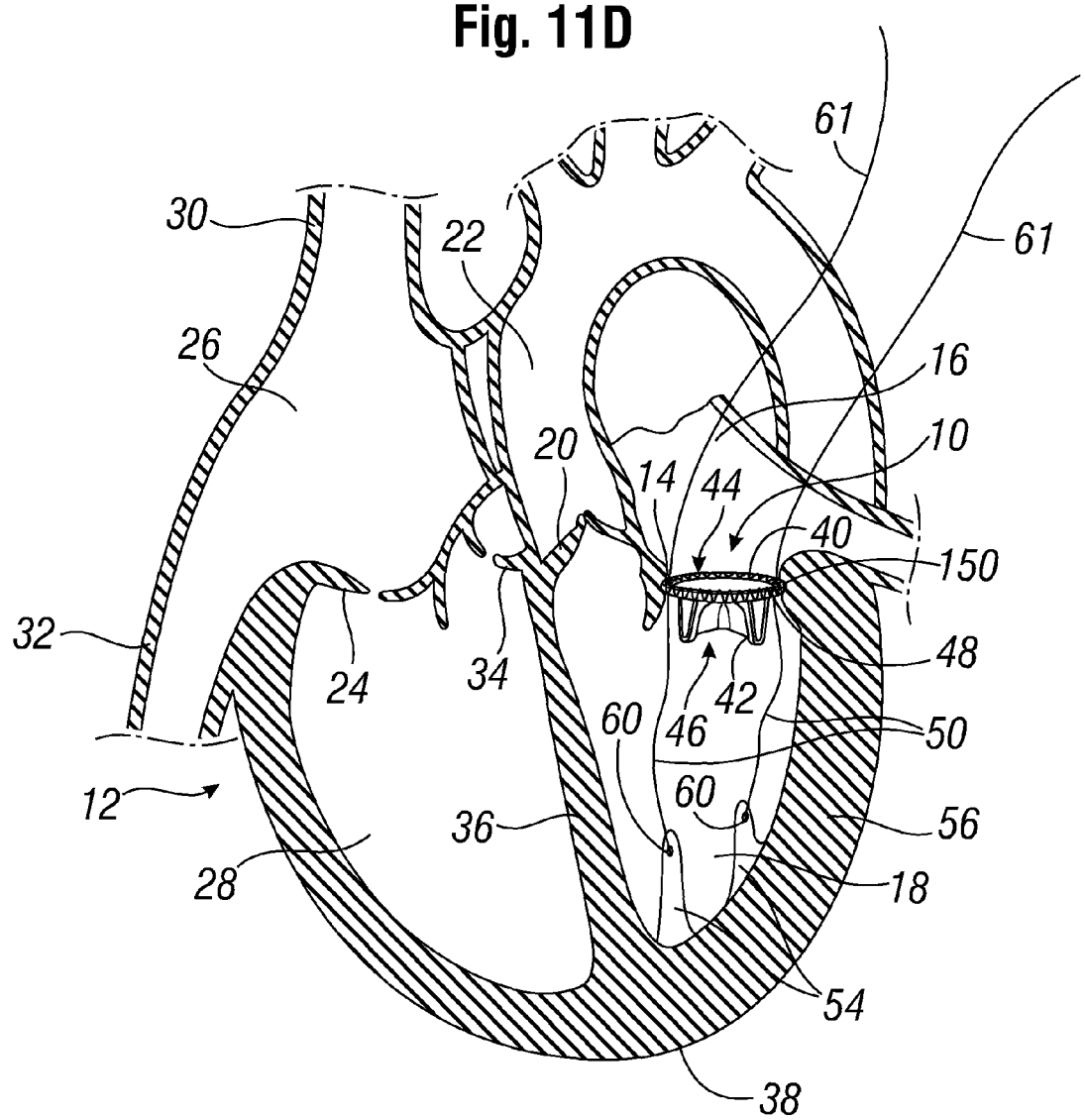

As depicted in FIG. 11D, the surgeon or other user may secure the prosthetic valve support frame to the native annulus via the sewing ring 48 and/or other an attachment structure configured to be attached to, and/or to otherwise facilitate securement of the device to, the annulus of a native heart valve. For example, the surgeon or other user may run multiple sutures 150 (e.g., 12-18 of such sutures) through the tissue of the native heart valve annulus 14 and through the sewing ring 48, and then tighten the sutures 150 to secure the support frame 40 securely the native heart valve annulus 14.

The surgeon or other user can adjust the usable length of (and accordingly the tension on) the tethers 50 to provide proper ventricular shaping for increased heart efficiency. This length adjustment can be performed entirely with the heart in an arrested condition (e.g., with the patient on bypass support), with the length adjustment finalized prior to resumption of heart beat. The length adjustment may be performed preliminarily with the heart in an arrested condition, with further refinements to the length made after the heart beat is restored. The length adjustment may alternatively be performed entirely after the heart beat is restored.

Figure 11E:
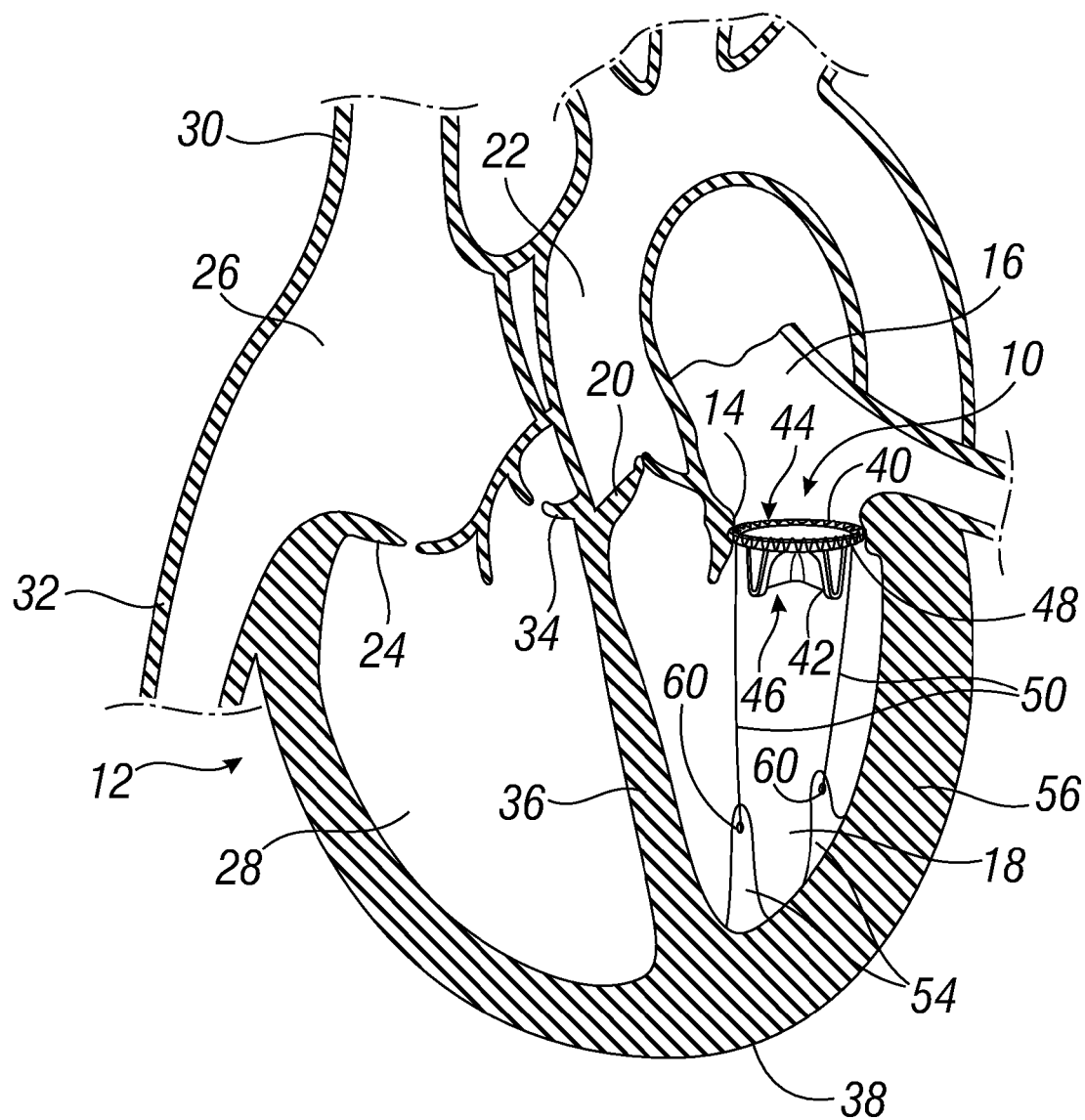

FIG. 11E depicts heart 12 with the procedure completed, and with the tethers 50 in their final tightened position with the ventricular wall 56 reshaped by the tethers 50.

Figure 12:
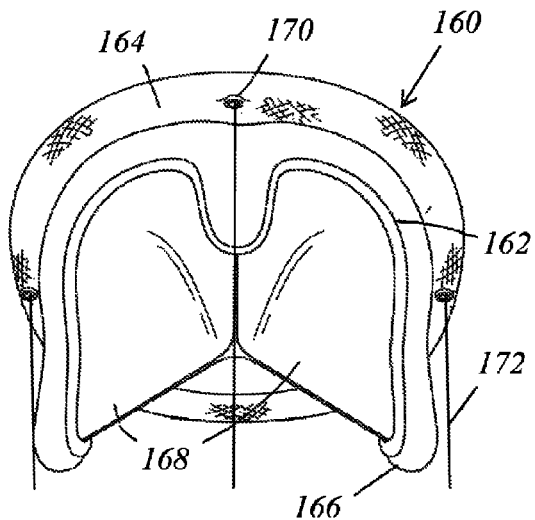
FIG. 12 is an outflow perspective view of an exemplary bioprosthetic heart valve having locking clips distributed around a sewing ring for securing tethers therethrough.

As mentioned above, the tethers 50 that attach to ventricular structure are secured either to the support frame or sewing ring of prosthetic mitral or tricuspid valves, such as at a locations adjacent the commissure posts. There are a number of ways to attach tethers to heart valves, such as by providing a cinch or other such fastener on the atrial side of the sewing ring, which can be advanced down the free length of the tether after adjusting the tension thereof. FIG. 12 is an outflow perspective view of an exemplary bioprosthetic mitral heart valve 160 including a support frame 162 having a sewing ring 164 around an inflow end, and a plurality of cantilevered commissure posts 166 extending in an outflow direction and supporting flexible leaflets 168 therebetween. A number of locking clips 170 are shown distributed around the sewing ring 164 for securing tethers 172.

FIG. 12 illustrates the tether locking clips 170 embedded within the suture-permeable sewing ring 164 of the heart valve 160. The sewing ring 164 typically has an inner silicone waffle enclosed within a fabric cover, although other configurations are known. Embedding the locking clips 170 into the sewing ring 164 is an integrated approach that simplifies delivery and deployment of the tethers 172 (i.e., there are no loose clips). Although there are three tether clips 170 shown distributed around the sewing ring 164 just outside of each of the commissure posts 166, a different number of clips such as two or six can be used, and they may be positioned at different locations.

Figure 13A:
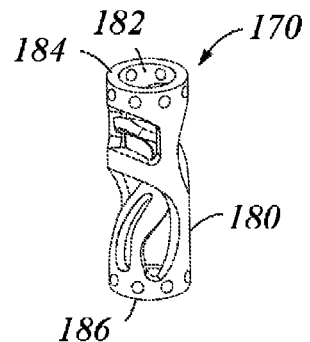
FIGS. 13A-13C are perspective and elevational views of an exemplary locking clip that can be embedded in the bioprosthetic heart valve of FIG. 12.
Figures 13B, 13C:
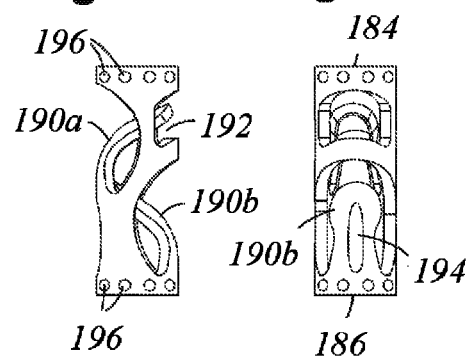

FIGS. 13A-13C show details of an exemplary locking clip 170 which has a generally tubular outer wall 180 defining a lumen 182 having a diameter extending from a proximal end 184 to a distal end 186. The outer wall 180 is interrupted by a collapsible wall structure for contacting and holding a tether 172 (e.g., a suture) passing through the lumen 182. As will be described, the collapsible wall structure has an open state that does not restrict relative movement between the locking clip 170 and a tether therein, and is biased toward a closed state that restricts relative distal movement of a tether through the clip without preventing relative proximal movement.

The tether locking clip 170 is preferably formed from an elastic material such as a memory material like Nitinol. The collapsible wall structure comprises a pair of tabs 190 cut into the tubular outer wall 180 each of which extends into the lumen 182 in the closed state. Each tether locking clip 170 further includes a window 192 in the tubular outer wall 180 opposite each of the tabs 190 and into which the respective opposed tab extends in the closed state of the fastener. More particularly, an upper tab 190a extends into an upper window 192 that is opposite from the upper tab. A lower tab 190b extends into a lower window that is formed in the upper tab 190a and not visible in the drawings. The lower window resembles a similar window 194 formed in the lower tab 190b. Two rows of small holes 196 are provided around the circumference of the outer wall 180 adjacent the proximal and distal ends 184, 186.

As will be clear from the explanation of use of the tether locking clip 170, the tabs 190 that are spring-biased inward clamp onto and restrict distal (downward) movement of a tether through the clip without preventing proximal (upward) movement. In practice, it is the tether locking clip 170 that moves relative to the fixed tether, such that even in the closed state the tabs 190 permit distal (downward) movement of the heart valve 160 on the tethers while preventing proximal (upward) movement. This permits a user to adjust a heart valve down an array of tethers pre-installed within the ventricle until the desired tension is reached, at which point, if not already done, the tether clips may be deployed to their closed states which prevents the heart valve from moving upward on the tethers and loosening the tension.

Figure 14A:
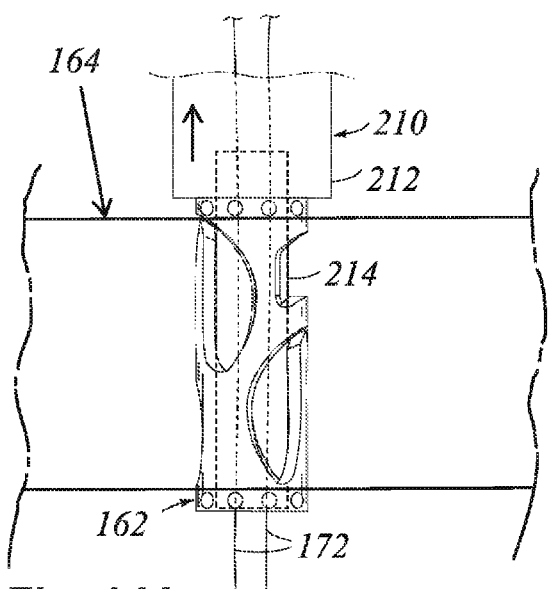
FIGS. 14A and 14B show one technique for actuating the exemplary locking clip of FIGS. 13A-13C.
Figure 14B:
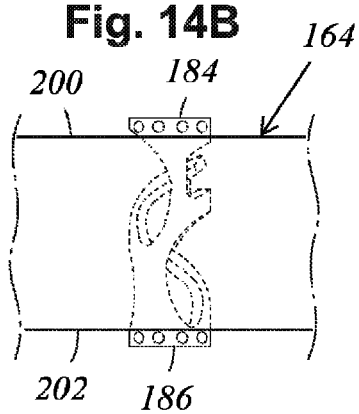

As seen in FIGS. 14A and 14B, the proximal end 184 of the tether locking clip 170 projects slightly above a proximal face 200 of the sewing ring 164, while the distal end 186 projects slightly below the distal face 202. In the case of a mitral or tricuspid heart valve, the proximal face 200 is on the inflow side of the sewing ring 164, and the distal face 202 is on the outflow side. The distance that the locking clip 170 can project from either face depend somewhat on the particular valve annulus at which the heart valve is secured, but typically neither end of the clip extends more than 3 mm above or below the sewing ring 164.

FIG. 14B shows an exemplary configuration for securing the tether locking clip 170 within the heart valve 160. In particular, a plurality of attachment threads (not numbered) loop through the small holes 196 at the proximal and distal ends 184, 186 and tie off through the fabric cover of the sewing ring 164. The tubular tether locking clip 170 may first be pushed through the soft sewing edge using a leading punch or awl-type of device (not shown). Other configurations for securing the tether locking clip 170 in the illustrated position within the heart valve 160 are contemplated. For example, flanges on either end may be provided which retain the clip in position, one of the flanges being spring-loaded so that it may first be retracted for insertion into the soft sewing ring 164.

FIGS. 14A and 14B illustrate an exemplary procedure for securing the tethers 172 relative to the sewing ring 164 of the heart valve 160. FIG. 14A shows an assembly of the sewing ring 164, the clips 170, and a deployment tube 210 for each fastener. Each deployment tube 210 includes a guide tube 212 and a smaller integrated hypotube 214 on a distal end. Each of the clips 170 receives a hypotube 214 in its lumen 182 that holds the resilient tabs 190 outward into their open state, and the guide tube 212 contacts the proximal end 184 of the clip. In this regard, each deployment tube 210 along with the hypotube 214 is preferably pre-assembled and packaged along with the heart valve 160 to avoid the process of connecting each of the deployment tubes to an associated clip 170 in the operating room. Alternatively, a mechanism (not shown) for rapidly loading each of the hypotubes into a respective suture clip 170 may be provided along with the packaged heart valve 160 to facilitate the assembly in the operating room.

In the embodiment of FIG. 14A, the hypotube 214 attaches within and projects from a distal end of a larger guide tube 212. Alternatively, the hypotube 214 may extend the full length of and be movable relative to the guide tube 212. The hypotube 214 has an outer diameter that is slightly smaller than the inner diameter of the tubular wall 180 of the suture clip 170, and as such, when inserted in the lumen 182, the hypotube maintains the tabs 190 flexed outward in the axial positions shown in FIG. 14A. After anchoring in a ventricular structure, or more tethers 172 may then be threaded through the hypotube 214 so is to pass from the outflow face 202 to the inflow face 200 of the sewing ring 164. Proximal displacement of the hypotube 214 such as from FIGS. 14A to 14B permits the tabs 190 to spring inward, thus clamping the tethers 172 and preventing proximal displacement of the clip 170 and associated sewing ring 164 relative thereto.

The materials used for the deployment tubes 210 are typical for surgical implant devices, including various non-corrosive metals, various grades and hardnesses of plastics, lubricious materials such as Teflon, silicone rubbers, etc. However, the hypotube 214 is desirably made of surgical grade metal such as stainless steel so that it maintains its diameter against the inward force of the fastener tabs 190 over potentially long periods of storage time. Further, a metal will better resist gouging by the tabs and can therefore be easily removed from within the clips 170.

It will be understood by the reader that the hypotube 214 cannot simply be inserted downward through the clip 170, because of the inwardly flexed tabs 190, but instead a thin assembly shaft (not shown) of the same size is first inserted upward to force the tabs 190 outward. Subsequently, the hypotube 214 is pushed downward through clip 170 so as to displace the assembly shaft without permitting the tabs 190 to spring inward. This can be done manually, but preferably a loading fixture to center the cooperating elements is used. Again, this can be done at the time of manufacture, or at the time of the heart valve replacement operation in the surgical theater.

Embodiments of the present disclosure may include methods of treating a heart with the heart treatment devices disclosed herein. As noted above, the devices and methods disclosed herein may be applicable to any heart valve, including, for example, the mitral valve and the tricuspid valve. In particular, although most of the embodiments disclosed herein are described relative to the left side of the heart (e.g., the left ventricle and the mitral valve), those of ordinary skill in the art will readily recognize that the embodiments of the present disclosure may have at least equal applicability to the right side of the heart (e.g., the right ventricle and the tricuspid valve).

The methods disclosed herein may be performed by any suitable surgical technique known in the art, including, but not limited to, open surgery, minimally invasive or non-invasive surgery, endoscopically, percutaneously, transapical, transaortic, transarterial, and/or any combination thereof. In one embodiment, it is contemplated that the devices disclosed herein may be implanted within a patient via, for example, a minimally invasive surgical technique known as a thoracotomy, such as, for example, an eight (8) centimeter thoracotomy. In other embodiments, the embodiments described herein may be implanted within a patient's heart via a transapical procedure. In addition, the methods described herein may be performed with or without the aid of cardiopulmonary bypass, as desired. For example, in one embodiment, the devices disclosed herein may be implanted and/or adjusted while heart function has been temporarily ceased and the patient is dependent upon cardiopulmonary bypass (i.e., on-pump). In another embodiment, however, the disclosed devices may be implanted and/or adjusted in accordance with the present disclosure without ceasing heart function (i.e., off-pump).

In one aspect of a method for treating a heart with the devices disclosed herein, a prosthetic heart valve assembly of the invention may be advanced into a patient's heart by any suitable methods known in the art. For example, prosthetic heart valve assembly may be advanced to a treatment site via any standard open-surgery technique. Alternatively, prosthetic heart valve assembly may be advanced to a treatment site via a transapical approach. Once at the desired treatment site, such as, for example, the mitral valve, support frame may be secured to the annulus of the mitral valve by any suitable means known in the art. For example, the support frame may be sewn via the sewing ring to the annulus of the mitral valve. Next, distal ends of elongate members and/or their associated anchors may be brought from the atrial side of the heart to the ventricular side by, for example, piercing the annulus of the mitral valve at positions corresponding to the points of exit of tethers. This piercing may be accomplished by any suitable means known in the art. For example, the annulus may be pierced by a surgical tool or by needles disposed at distal ends of tethers and/or on the anchors. Instead of piercing the annulus of mitral valve, however, the principles of the present disclosure also provide for simply extending elongate members through mitral valve annulus and into the left ventricle. Once within left ventricle, distal ends and/or associated anchors may be secured to heart structure, such as, for example, the papillary muscles or a heart wall, in accordance with the embodiments described above. In some instances, securing distal ends of tethers to heart structure may cause tethers to undergo elongation. For example, the principles of the present invention contemplate a tether elongation of up to 30% in some embodiments. In other embodiments, the elongation experienced by tethers may be approximately 5-7% or even down to about zero.

Once support frame and tethers have been appropriately secured to targeted heart tissue, the heart may be surgically closed, its cavities evacuated from air and allowed to fill with blood, and normal heart rhythm may be resumed. Stated differently, the patient may be taken off of cardiopulmonary bypass. Subsequently, under guidance afforded by any suitable imaging technique, such as, for example, transesophageal echocardiography, the usable length of tethers may be adjusted such as by advancing an actuating tool to engage and activate/deactivate the locking mechanism(s). To facilitate suitable imaging, those of ordinary skill in the art will recognize that the embodiments disclosed herein may be provided with one or more appropriately located visible markers, such as, for example, radiopaque markers.

In particular, the principles of the present disclosure provide for drawing the posterior papillary muscle inwards laterally and/or vertically by approximately thirty (30) millimeters. The anterior papillary muscle may be drawn inwards laterally and/or vertically by approximately ten (10) millimeters. Finally, the usable lengths of tethers may be adjusted to be between approximately ten (10) to forty (40) millimeters. As a result of one or more of these adjustments, the papillary muscles may be drawn closer together by approximately twenty (20) millimeters. Further, a shape of the heart chamber (e.g., left or right ventricle) may be altered. As those of ordinary skill in the art will readily recognize, all of these adjustments may be made simultaneously by, for example, rotating locking mechanism with actuating tool. In accordance with the principles of the present disclosure, adjusting tether usable length in the aforementioned manner while the heart is beating may afford an operator the opportunity to identify improper heart valve function and finely tune the prosthetic heart valve assembly to address inaccuracies not otherwise addressable by non-adjustable heart treatment devices.

The aforementioned adjustments to the prosthetic heart valve assembly may be made at any suitable time. For example, prosthetic heart valve assembly may be adjusted during an implantation procedure. In addition, or alternatively, prosthetic heart valve assembly may be adjusted shortly after implantation, such as, for example, between two (2) to ten (10) days after implantation. Furthermore, prosthetic heart valve assembly may be adjusted again at any time necessary, such as, for example, six (6) months or one (1) year after implantation.

The tethers may be made of any suitable biocompatible material, such as traditional suture material, GORE-TEX®, or an elastomeric material, such as polyurethane.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope of these claims.

What is claimed is:

1. A device for treating a heart, comprising:
  a prosthetic valve comprising a support frame and a valve portion, the valve portion comprising a plurality of leaflets secured to the support frame and configured to coapt to permit blood flow in a first direction through the valve portion and to prevent blood flow in a second direction through the valve portion, wherein the first direction is opposite to the second direction, wherein the support frame comprises a sewing ring configured to be sutured at least one to tissue of an annulus of a native heart valve;
  a plurality of locking clips embedded within the sewing ring of the heart valve;
  a plurality of tethers, each tether passing through one of the plurality of locking clips, wherein a distal end of each tether has a tissue anchor configured to be secured to heart geometry within a ventricular chamber of the heart, wherein each tether comprises a usable length from the respective locking clip support frame to the distal end; and
  a hollow hypotube we-assembled within each of the locking clips, wherein removing the hypotube from its respective locking clip causes the respective tether to be fixed within the locking clip, wherein each locking clip comprises an adjustment mechanism for the corresponding tether for altering the usable length of the tether.

2. The device of claim 1, wherein each locking clip includes a tubular body with a collapsible wall structure.

3. The device of claim 1, wherein each locking clip includes a collapsible structure which selectively fixes the corresponding tether therein.

4. The device of claim 1, wherein a larger guide tube is integrated with each hypotube, and each of the locking clips receives the hypotube in its lumen with the guide tube contacting a proximal end of the locking clip.

5. The device of claim 1, wherein the tethers are selected from the group consisting of: a shape memory alloy, a flexible metal or polymer.

6. A device for treating a heart, comprising:
  a prosthetic valve comprising a support frame and a valve portion, the valve portion comprising a plurality of flexible leaflets secured to the support frame and configured to coapt to permit blood flow in a first direction through the valve portion and to prevent blood flow in a second direction through the valve portion, wherein the first direction is opposite to the second direction, wherein the support frame further includes commissure posts to which adjacent leaflets attach and a sealing ring located radially outward from the commissure posts and configured to be sealed against tissue of an annulus of a native heart valve;
  a plurality of elongate members adjustably secured around the support frame and passing through the sealing ring, wherein a distal end of each elongate member has a tissue anchor configured to be secured to heart geometry within a ventricular chamber of the heart, wherein each elongate member comprises a usable length from the support frame to the distal end of between about 10-40 mm; and
  a plurality of locking clips embedded within the sealing ring through each of which passes one of the elongate members, each locking clip including a collapsible structure which selectively fixes the corresponding elongate member therein, and a hollow hypotube pre-assembled within each of the locking clips, wherein removing the hypotube from its respective locking clip releases the collapsible structure and causes the elongate member to be fixed within the locking clip, wherein each locking clip comprises an adjustment mechanism for the corresponding elongate member for altering the usable length of the elongate member.

7. The device of claim 6, wherein a larger guide tube is integrated with each hypotube, and each of the locking clips receives the hypotube in its lumen with the guide tube contacting a proximal end of the locking clip.

8. The device of claim 6, wherein the tissue anchor includes structure that embeds into the heart geometry.

9. The device of claim 8, wherein the tissue anchor is selected from the group consisting of: a corskscrew-like member, a loop configured to be sewn to tissue, and a series of curled barbs that deploy outward from a straightened configuration when expelled from a delivery tube.

10. The device of claim 6, wherein the tissue anchor includes structure configured to extend transmurally to a support pad adapted to be in contact with an outside surface of the ventricle.

11. The device of claim 6, further including brush guards extending from and between the commissure posts of the support frame to create a fence-like enclosure about the flexible leaflets.

12. The device of claim 6, wherein the locking clips are embedded within the sealing ring at positions adjacent a commissure post.

13. The device of claim 6, wherein the elongate members each comprises a tether.

* * * * *